United States Patent [19]

Katsura et al.

[11] Patent Number: 5,532,258
[45] Date of Patent: Jul. 2, 1996

[54] $H_2$-RECEPTOR ANTAGONIST THIAZOLES

[75] Inventors: Yousuke Katsura, Toyonaka; Tetsuo Tomishi, Minoo; Yoshikazu Inoue, Amagasaki; Hisashi Takasugi, Sakai, all of Japan

[73] Assignee: Fujisawa Pharmaceutical Co., Ltd., Osaka, Japan

[21] Appl. No.: 356,967

[22] Filed: Dec. 16, 1994

Related U.S. Application Data

[63] Continuation of Ser. No. 978,477, Nov. 18, 1992, abandoned.

[30] Foreign Application Priority Data

Dec. 6, 1991 [GB] United Kingdom ............... 9125970

[51] Int. Cl.⁶ .................. C07D 277/48; A61K 31/125
[52] U.S. Cl. ................ 514/370; 548/193; 548/194; 548/198
[58] Field of Search ................ 548/194, 198, 548/193; 514/370

[56] References Cited

U.S. PATENT DOCUMENTS 4,315,009  2/1982  Jones ........................... 514/370

*Primary Examiner*—Robert Gerstl
*Attorney, Agent, or Firm*—Oblon, Spivak, McClelland, Maier & Neustadt

[57] ABSTRACT

Thiazole compounds of formula

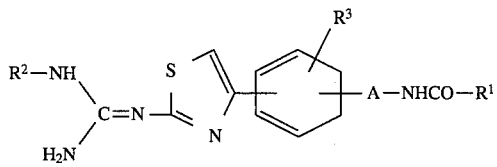

are provided which have antiulcer activity and $H_2$-receptor antagonism, wherein $R^2$ is lower alkyl or lower alkoxy(lower)alkyl, $R^3$ is hydrogen, A is methylene and $R^1$ is lower alkyl.

5 Claims, No Drawings

$H_2$-RECEPTOR ANTAGONIST THIAZOLES

This is a continuation of application Ser. No. 07/978,477 filed on Nov. 18, 1992, now abandoned.

This invention relates to new compounds and pharmaceutically acceptable salts thereof.

More particularly, it relates to new thiazole derivatives and pharmaceutically acceptable salts thereof which have antiulcer activity and $H_2$-receptor antagonism, to processes for the preparation thereof, to a pharmaceutical composition comprising the same and to a method for the treatment of ulcer in human being or animals.

Accordingly, one object of this invention is to provide new thiazole derivatives and pharmaceutically acceptable salts thereof which possess antiulcer activity and $H_2$-receptor antagonism.

Another object of this invention is to provide processes for the preparation of said thiazole derivatives and salt thereof.

A further object of this invention is to provide a pharmaceutical composition comprising, as an active ingredient, said thiazole derivatives or pharmaceutically acceptable salts thereof.

Still further object of this invention is to provide a method for the prophylactic or therapeutic treatment of ulcer in human being or animals.

The thiazole derivatives of this invention are new and can be represented by the following general formula (I):

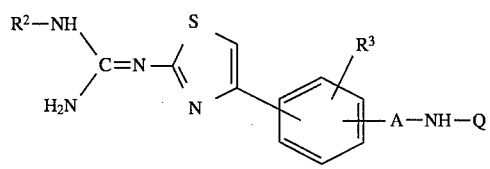

wherein $R^2$ is hydrogen, or lower alkyl which may have suitable substituent(s), $R^3$ is hydrogen, lower alkyl, lower alkoxy, or halogen, A is lower alkylene and Q is a group of the formula:

—CO—$R^1$ (in which $R^1$ is an organic group), or carbamimidoyl which may have suitable substituent(s), with proviso that when Q is carbamimidoyl which may have suitable substituent(s), then R is lower alkoxy.

The object compound (I) or a salt thereof can be prepared by processes as illustrated in the following reaction schemes.

Process (1)

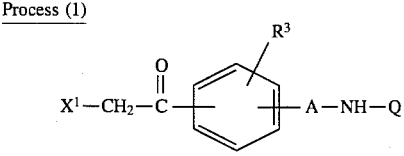

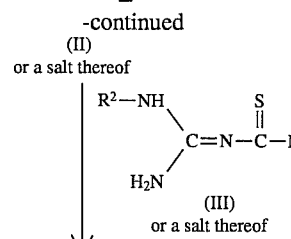
(II)
or a salt thereof (III)
or a salt thereof

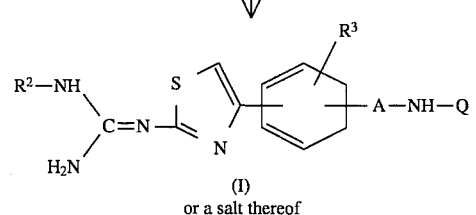
(I)
or a salt thereof

Process (2)

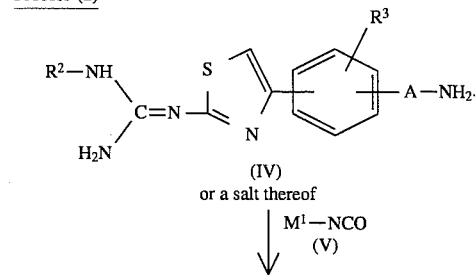
(IV)
or a salt thereof

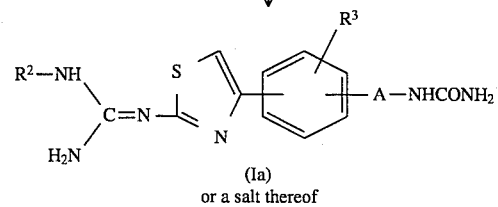
(Ia)
or a salt thereof

Process (3)

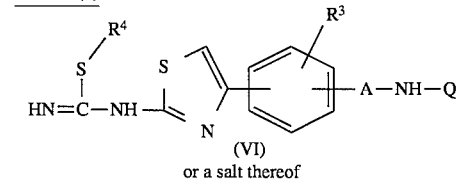
(VI)
or a salt thereof

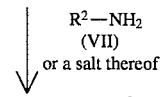
$R^2$—$NH_2$
(VII)
or a salt thereof

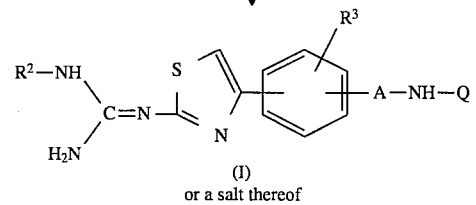
(I)
or a salt thereof

Process (4)

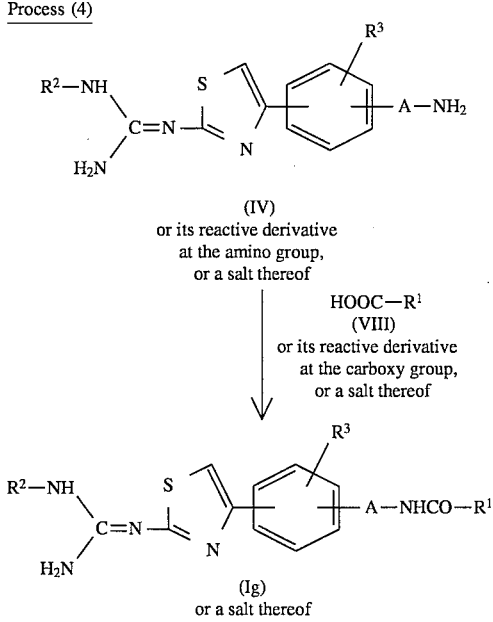

Process (5)

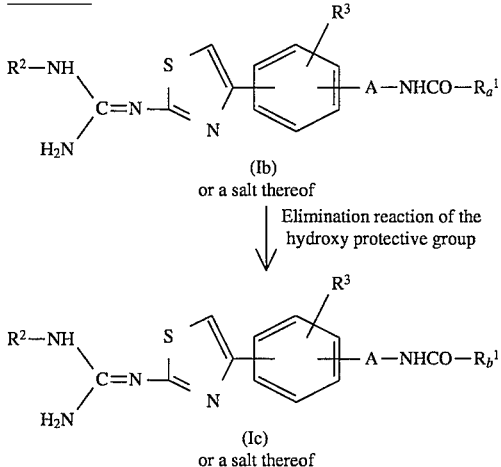

Process (6)

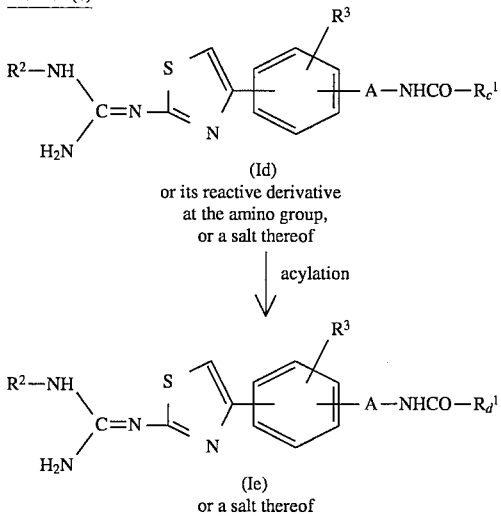

Process (7)

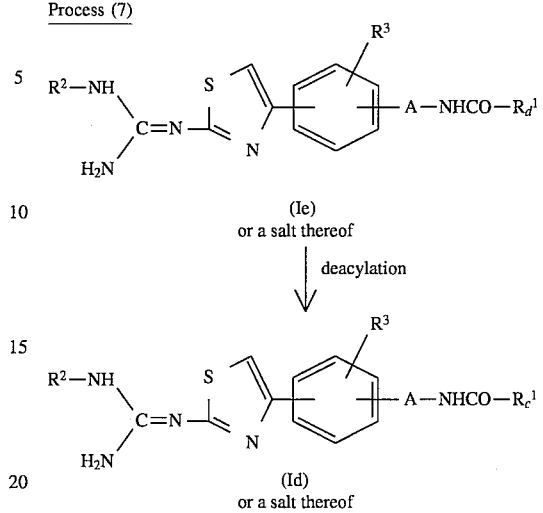

Process (8)

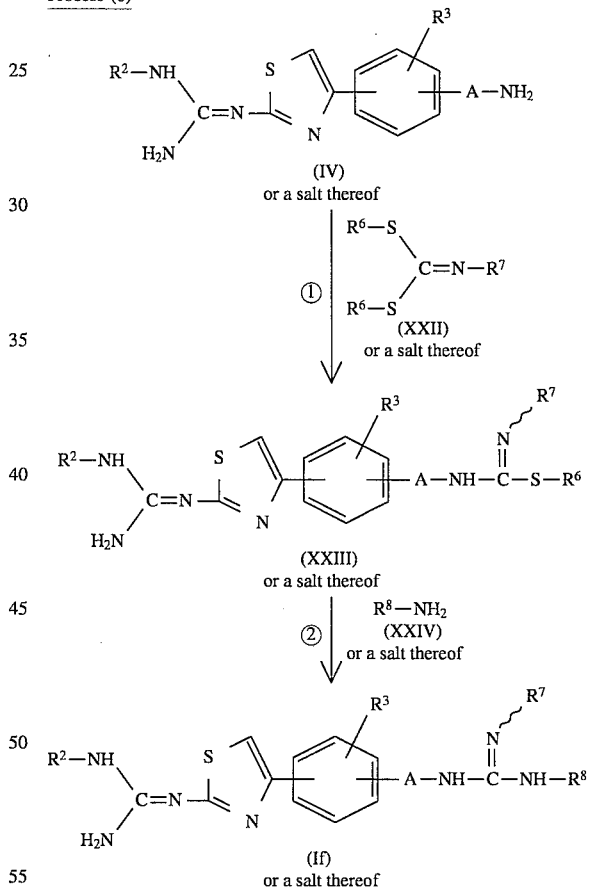

wherein $R^1$, $R^2$, $R^3$, A and Q are each as defined above
$R^4$ and $R^6$ are each lower alkyl,
$R^7$ and $R^8$ are each substituent,
$R_a^1$ is protected hydroxy(lower)alkyl,
$R_b^1$ is hydroxy(lower)alkyl, $R_c^1$ is amino(lower)alkyl,
$R_d^1$ is acylamino(lower)alkyl, $X^1$ is acid residue, and
$M^1$ is an alkali metal.

The starting compounds (II), (IV) and (VI) or salts thereof can be prepared by the following Processes.

Process (A)
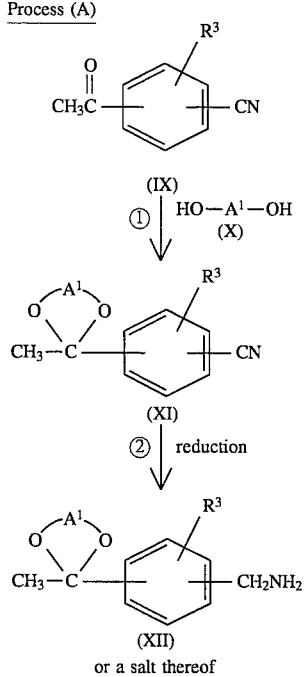
Process (B)
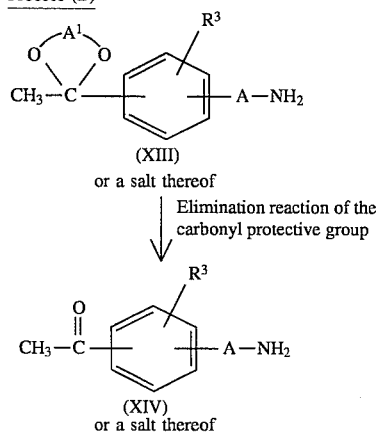
Process (C)
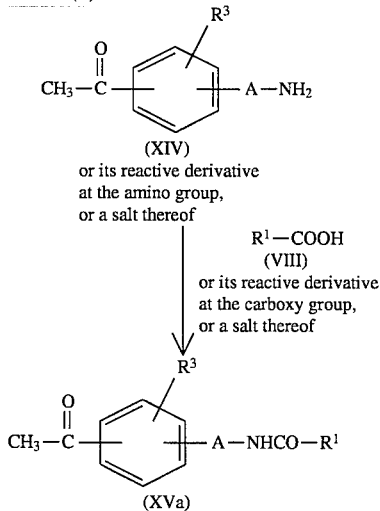
Process (D)
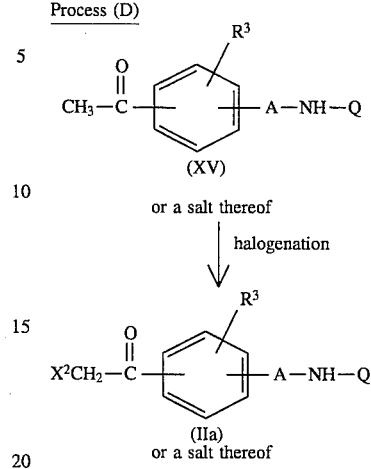
Process (E)
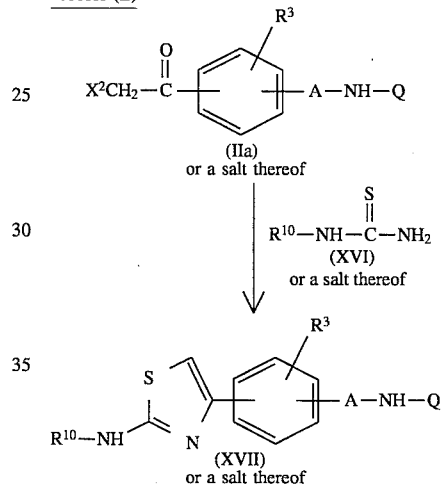
Process (F)
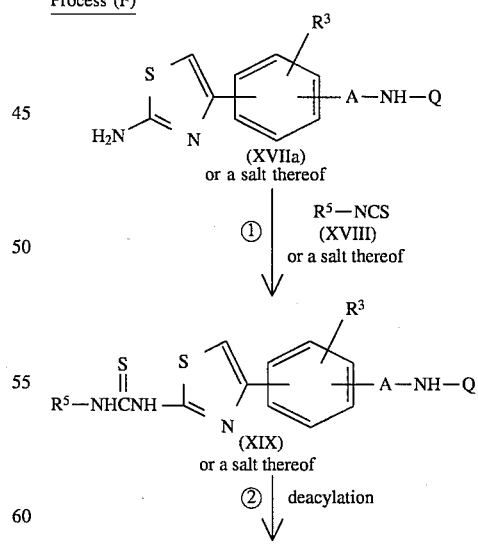

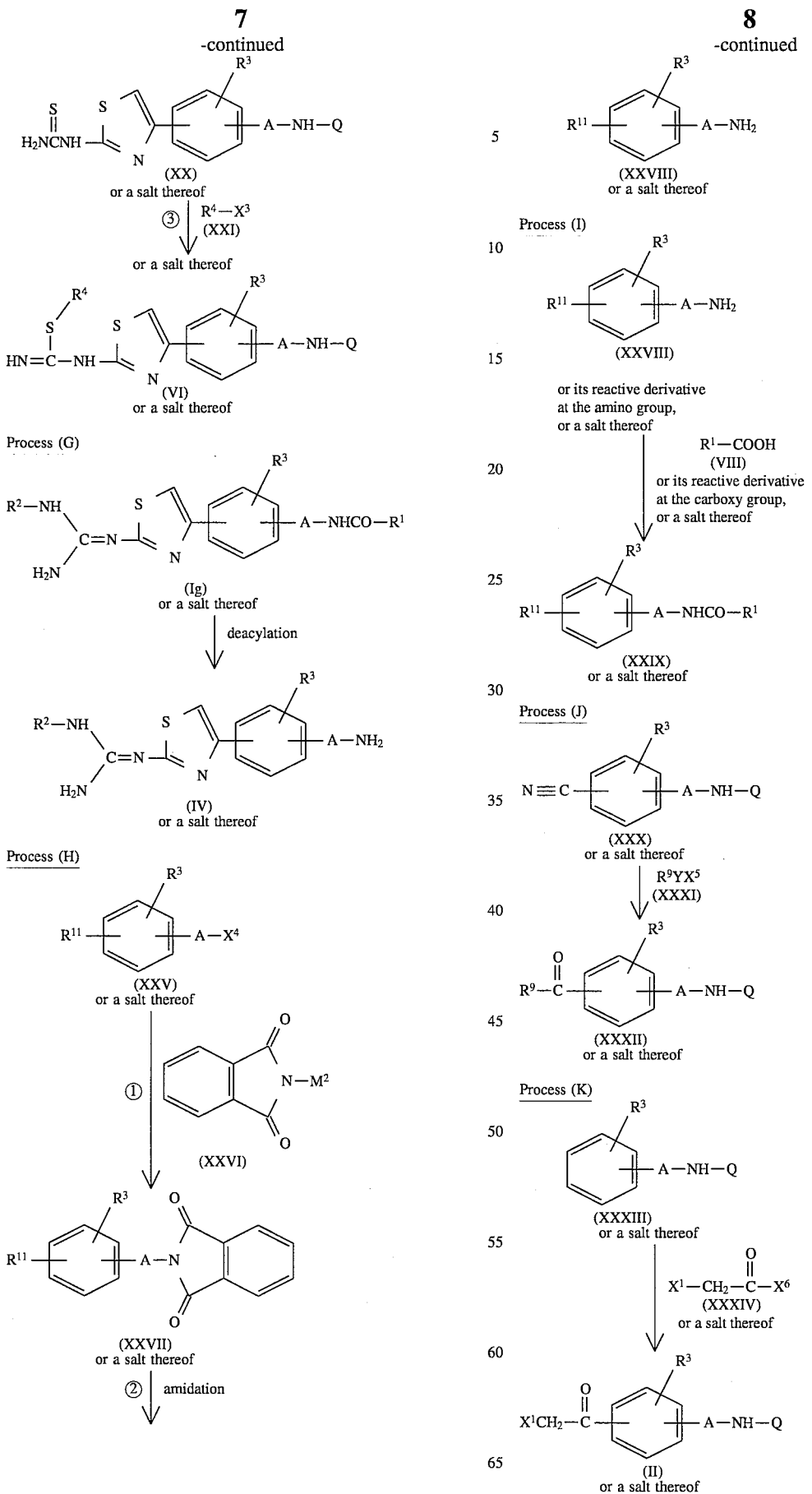

wherein $R^1$, $R^2$, $R^3$, $R^4$, $X^1$, A and Q are each as defined above, $R^5$ is acyl, $R^9$ is lower alkyl, $R^{10}$ is hydrogen or thiocarbamoyl, $R^{11}$ is cyano or lower alkanoyl, Y is an alkaline earth metal, $A^1$ is lower alkylene, $M^2$ is an alkali metal, $X^2$ and $X^5$ are each halogen and $X^3$, $X^4$ and $X^6$ are each acid residue.

Suitable pharmaceutically acceptable salts of the object compound (I) are conventional non-toxic salts and may include e.g. a salt with a base or an acid addition salt such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.); an inorganic acid addition salt (e.g. hydrochloride, hydriodide, hydrobromide, sulfate, phosphate, etc.); an organic carboxylic or sulfonic acid addition salt (e.g. formate, acetate, trifluoroacetate, maleate, tartrate, methanesulfonate, benzenesulfonate, toluenesulfonate, etc.); a salt with a basic or acidic amino acid (e.g. arginine, aspartic acid, glutamic acid, etc.).

In the above and subsequent descriptions of the present specification, suitable example and illustration of the various definitions which the present invention intends to include within the scope thereof are explained in detail as follows.

The term "lower" is used to intend a group having 1 to 6, preferably 1 to 4, carbon atom(s), unless otherwise provided.

The term "higher" is used to intend a group having 7 to 20 carbon atoms unless otherwise provided.

Suitable "organic group" may include lower alkyl (e.g., methyl, ethyl, propyl, isopropyl, butyl, isobutyl, tert-butyl, pentyl, neopentyl, tert-pentyl, hexyl, etc.), hydroxy(lower)alkyl, protected hydroxy(lower)alkyl, lower alkoxy (e.g. methoxy, ethoxy, propoxy, isopropoxy, butoxy, isobutoxy, t-butoxy, pentyloxy, t-pentyloxy, hexyloxy, etc.), amino, amino(lower)alkyl, protected amino(lower)alkyl, lower alkenyl (e.g., vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.), lower alkynyl (e.g., ethynyl, 1-propynyl, propargyl, 1-methylpropargyl, 1 or 2 or 3-butynyl, 1 or 2 or 3 or 4-pentynyl, 1 or 2 or 3 or 4 or 5-hexynyl, etc.), aryl (e.g., phenyl, naphthyl, etc.), ar(lower)alkyl such as phenyl(lower)alkyl (e.g., benzyl, phenethyl, phenylpropyl, etc.), and the like.

Suitable "lower alkyl" and "lower alkyl moiety" in the terms "hydroxy(lower)alkyl", "protected hydroxy(lower)alkyl", "amino(lower)alkyl", "acylamino(lower)alkyl" and "protected amino(lower)alkyl" may include straight or branched one such as methyl, ethyl, propyl, isopropyl, butyl, t-butyl, pentyl, hexyl, and the like, in which more preferable example may be $C_1$–$C_4$ alkyl.

Suitable "substituent" in the term "lower alkyl which may have suitable substituent(s)" may include lower alkyl (e.g., methyl, ethyl, propyl, isopropyl, butyl, isobutyl, t-butyl, pentyl, neopentyl, t-pentyl, hexyl, etc.), lower alkoxy (e.g., methoxy, ethoxy, propoxy, isopropoxy, isobutoxy, t-butoxy, pentyloxy, neopentyloxy, t-pentyloxy, hexyloxy, etc.), lower alkenyl (e.g., vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.), lower alkynyl (e.g., ethynyl, 1-propynyl, propargyl, 1-methylpropargyl, 1-methylpropargyl, 1 or 2 or 3-butynyl, 1 or 2 or 3 or 4-pentynyl, 1 or 2 or 3 or 4 or 5-hexynyl, etc.), mono(or di or tri)halo(lower)alkyl (e.g., fluoromethyl, difluoromethyl, trifluoromethyl, chloromethyl, dichloromethyl, trichloromethyl, bromomethyl, dibromomethyl, tribromomethyl, 1 or 2-fluoroethyl, 1 or 2-bromoethyl, 1 or 2-chloroethyl, 1,1-difluoroethyl, 2,2-difluoroethyl, etc.), halogen (e.g., chlorine, bromine, fluorine, iodine), carboxy, protected carboxy, hydroxy, protected hydroxy, aryl (e.g., phenyl, naphthyl, etc.) which may have suitable substituent(s) (e.g., lower alkyl, lower alkenyl, lower alkynyl, lower alkoxy, etc.), ar(lower)alkyl such as phenyl(lower)alkyl (e.g., benzyl, phenethyl, phenylpropyl, etc.), carboxy(lower)alkyl, protected carboxy(lower)alkyl, nitro, amino, protected amino, di(lower)alkylamino (e.g., dimethylamino, diethylamino, diisopropylamino, ethylmethylamino, isopropylmethylamino, ethylmethylamino, ethylpropylamino, etc.), hydroxy(lower)alkyl, protected hydroxy(lower)alkyl, acyl, cyano, mercapto, lower alkylthio (e.g., methylthio, ethylthio, propylthio, isopropylthio, butylthio, etc.), imino, heterocyclic group, and the like.

Suitable "substituent" for $R^7$ and $R^8$ and "substituent" in the term "carbamimidoyl which may have suitable substituent(s)" may include lower alkyl (e.g., methyl, ethyl, propyl, isopropyl, butyl, isobutyl, t-butyl, pentyl, neopentyl, t-pentyl, hexyl, etc.), lower alkoxy (e.g., methoxy, ethoxy, propoxy, isopropoxy, isobutoxy, t-butoxy, pentyloxy, neopentyloxy, t-pentyloxy, hexyloxy, etc.), lower alkenyl (e.g., vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.), lower alkynyl (e.g., ethynyl, 1-propynyl, propargyl, 1-methylpropargyl, 1-methylpropargyl, 1 or 2 or 3-butynyl, 1 or 2 or 3 or 4-pentynyl, 1 or 2 or 3 or 4 or 5-hexynyl, etc.), mono(or di or tri)halo(lower)alkyl (e.g., fluoromethyl, difluoromethyl, trifluoromethyl, chloromethyl, dichloromethyl, trichloromethyl, bromomethyl, dibromomethyl, tribromomethyl, 1 or 2-fluoroethyl, 1 or 2-bromoethyl, 1 or 2-chloroethyl, 1,1-difluoroethyl, 2,2-difluoroethyl, etc.), halogen (e.g., chlorine, bromine, fluorine, iodine), carboxy, protected carboxy, hydroxy, protected hydroxy, aryl (e.g., phenyl, naphthyl, etc.), ar(lower)alkyl such as phenyl(lower)alkyl (e.g., benzyl, phenethyl, phenylpropyl, etc.), carboxy(lower)alkyl, protected carboxy(lower)alkyl, nitro, amino, protected amino, di(lower)alkylamino (e.g., dimethylamino, diethylamino, diisopropylamino, ethylmethylamino, isopropylmethylamino, ethylmethylamino, ethylpropylamino, etc.), hydroxy(lower)alkyl, protected hydroxy(lower)alkyl, acyl, cyano, mercapto, lower alkylthio (e.g., methylthio, ethylthio, propylthio, isopropylthio, butylthio, etc.), imino, and the like.

Suitable "protected amino moiety" in the term "protected amino(lower)alkyl" may include acylamino and the like.

Suitable "protected hydroxy" and "protected hydroxy moiety" in the term "protected hydroxy(lower)alkyl" may include acyloxy and the like.

Suitable "acyl" and "acyl moiety" in the terms "acylamino", "acyloxy" and "acylamino(lower)alkyl" may include carbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows:

carbamoyl;

Aliphatic acyl such as lower or higher alkanoyl (e.g. formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.);

lower or higher alkoxycarbonyl (e.g. methoxycarbonyl, ethoxycarbonyl, t-butoxycarbonyl, t-pentyloxycarbonyl, heptyloxycarbonyl, etc.);

lower or higher cycloalkylcarbonyl (e.g. cyclopropylcarbonyl, cyclobutylcarbonyl, cyclopentylcarbonyl, cyclohenylcarbonyl, etc.);

lower or higher alkylsulfonyl (e.g. methylsulfonyl, ethylsulfonyl, etc.);

lower or higher alkoxysulfonyl (e.g. methoxysulfonyl, ethoxysulfonyl, etc.); or the like;

Aromatic acyl such as aroyl (e.g. benzoyl, toluoyl, naphthoyl, etc.);

ar(lower)alkanoyl [e.g. phenyl(lower)alkanoyl (e.g. phenylacetyl, phenylpropanoyl, phenylbutanoyl, phenylisobutylyl, phenylpentanoyl, phenylhexanoyl, etc.), naphthyl(lower)alkanoyl (e.g. naphthylacetyl, naphthylpropanoyl, naphthylbutanoyl, etc.), etc.];

ar(lower)alkenoyl [e.g. phenyl(lower)alkenoyl (e.g. phenylpropenoyl, phenylbutenoyl, phenylmethacryloyl, phenytpentenoyl, phenylhexenoyl, etc.), naphthyl(lower)alkenoyl (e.g. naphthylpropenoyl, naphthylbutenoyl, naphthylpentenoyl, etc.), etc];

ar(lower)alkoxycarbonyl [e.g. phenyl(lower)alkoxycarbonyl (e.g. benzyloxycarbonyl, etc.), etc.];

aryloxycarbonyl (e.g. phenoxycarbonyl, naphthyloxycarbonyl, etc.);

aryloxy(lower)alkanoyl (e.g. phenoxyacetyl, phenoxypropionyl, etc.);

arylcarbamoyl (e.g. phenylcarbamoyl, etc.);

arylthiocarbamoyl (e.g. phenylthiocarbamoyl, etc.);

arylglyoxyloyl (e.g. phenylglyoxyloyl, naphthylglyoxyloyl, etc.);

arylsulfonyl (e.g. phenylsulfonyl, naphthylsulfonyl, etc.); or the like;

Heterocyclic acyl such as heterocycliccarbonyl;

heterocyclic(lower)alkanoyl (e.g. thienylacetyl, thienylpropanoyl, thienylbutanoyl, thienylpentanoyl, thienylhexanoyl, thiazolylacetyl, thiadiazolylacetyl, tetrazolylacetyl, etc.);

heterocyclic(lower)alkenoyl (e.g. heterocyclicpropenoyl, heterocyclicbutenoyl, heterocyclicpentenoyl, heterocyclichexenoyl, etc.);

heterocyclicglyoxyloyl (e.g. thiazolylglyoxyloyl, thienylglyoxyloyl, etc.); or the like.

Suitable "heterocyclic group" and "heterocyclic moiety" in the terms "heterocycliccarbonyl", "heterocyclic(lower)alkanoyl", heterocyclic(lower)alkenoyl and "heterocyclicglyoxyloyl" means saturated or unsaturated, monocyclic or polycyclic heterocyclic group containing at least one heteroatom such as an oxygen, sulfur, nitrogen atom and the like. And, especially preferable heterocyclic group may be heterocyclic group such as unsaturated 3 to 8-membered more preferably 5 or 6-membered heteromonocyclic group containing 1 to 4-nitrogen atom(s), for example, pyrrolyl, pyrrolinyl, imidazolyl, pyrazolyl, pyridyl and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

saturated 3 to 8-membered (more preferable 5 or 6-membered)heteromonocyclic group containing 1 to 4 nitrogen atom(s), for example pyrrolidinyl, imidazolidinyl, piperidinino, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, dihydroquinolyl, isoquinolyl, indazolyl, benzotriazolyl, etc.;

unsaturated 3 to 8-membered (more preferably 5 or 6-membered)heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.) etc.;

saturated 3 to 8-membered (more preferably 5 or 6-membered)heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered)heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithionyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 to 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydroxathiinyl, etc.;

unsaturated condensed heterocyclic group containing 1 to 2 sulfur atom(s), for example benzothienyl (e.g. benzo[b]thienyl, etc.), benzodithiinyl, etc.;

unsaturated condensed heterocyclic group containing an oxygen atom and 1 to 2 sulfur atom(s), for example, benzoxathiinyl, etc. and the like.

The acyl moiety as stated above may have one to five, same or different, suitable substituent(s) such as halogen (e.g. fluorine, chlorine, bromine or iodine), lower alkyl (e.g. methyl, ethyl, propyl, isopropyl, butyl, isobutyl, t-butyl, pentyl, hexyl, etc.);

lower alkoxy (e.g. methoxy, ethoxy, propoxy, isopropoxy, butoxy, isobutoxy, t-butoxy, pentyloxy, hexyloxy, etc.), hydroxy, carboxy, protected hydroxy, protected carboxy, mono(or di or tri)halo(lower)alkyl, N,N-di(lower)alkylamino (e.g. N,N-dimethylamino, N,N-diethylamino, N,N-dipropylamino, N,N -dibutylamino, N,N-dipentylamino, N,N-dihexylamino, N-methyl-N-ethylamino, N-methyl-N-butylamino, etc. ), or the like.

Suitable "alkali metal" may include lithium, sodium, potassium and the like.

Suitable "alkaline earth metal" may include magnesium, calcium and the like.

Suitable "acid residue" may include halogen (e.g., fluorine, chlorine, bromine, iodine), acyloxy [e.g., sulfonyloxy (e.g., phenylsulfonyloxy, tosyloxy, mesyloxy, etc.), lower alkanoyloxy (e.g., acetyloxy, propionyloxy, etc.), etc.] and the like.

Suitable "halogen" may include fluorine, bromine, chlorine and iodine.

Suitable "lower alkoxy" may include methoxy, ethoxy, propoxy, isopropoxy, butoxy, isobutoxy, t-butoxy, pentyloxy, t-pentyloxy, hexyloxy and the like.

Suitable "lower alkanoyl" may include formyl, acetyl, propanoyl, butanoyl, 2-methylpropanoyl, pentanoyl, 2,2-dimethylpropanoyl, hexanoyl and the like.

Suitable "lower alkylene" may include straight or branched one such as methylene, ethylene, trimethylene, tetramethylene, pentamethylene, hexamethylene, methylmethylene, ethylethylene, propylene, and the like, in which more preferable example may be $C_1$–$C_4$ alkylene.

The processes for preparing the object and starting compounds are explained in detail in the following.

Process (1)

The compound (I) or a salt thereof can be prepared by reacting the compound (II) or a salt thereof with the compound (III) or a salt thereof.

The reaction is usually carried out in a conventional solvent such as alcohol (e.g., methanol, ethanol, etc.), tetrahydrofuran, N,N-dimethylformamide, dichloromethane, acetone, acetic acid, or any other solvent which does not adversely influence the reaction.

The reaction temperature is not critical and the reaction is usually carried out under warming to heating.

Process (2)

The compound (Ia) or a salt thereof can be prepared by reacting the compound (IV) or a salt thereof with the compound (V).

The reaction is usually carried out in a conventional solvent such as water, alcohol (e.g., methanol, ethanol, isopropyl alcohol, t-butyl alcohol, etc.), tetrahydrofuran, dioxane, dichloromethane, chloroform, dimethyl acetamide, decalin, tetralin, N,N-dimethylformamide or any other organic solvent which does not adversely influence the reaction. Among these solvents, hydropholic solvents may be used in a mixture with water.

The reaction temperature is not critical and the reaction is usually carried out under cooling to warming.

Process (3)

The compound (I) or a salt thereof can be prepared by reacting the compound (VI) or a salt thereof with the compound (VII) or a salt thereof.

This reaction is usually carried out in a solvent such as alcohol (e.g. methanol, ethanol, etc.), benzene, N,N-dimethylformamide, tetrahydrofuran, methylene chloride, ethylene chloride, chloroform, diethyl ether or any other solvent which does not adversely affect the reaction.

The reaction temperature is not critical and the reaction is usually carried out under warming to heating.

Process (4)

The compound (Ig) or a salt thereof can be prepared by reacting the compound (IV) or its reactive derivative at the amino group, or a salt thereof with the compound (VIII) or its reactive derivative at the carboxy group, or a salt thereof.

Suitable reactive derivative at the amino group of the compound (IV) may include Schiff's base type imino or its tautomeric enamine type isomer formed by the reaction of the compound (IV) with a carbonyl compound such as aidehyde, ketone or the like; a silyl derivative formed by the reaction of the compound (IV) with a silyl compound such as bis(trimethylsilyl)acetamide, mono(trimethylsilyl)acetamide [e.g. N-(trimethylsilyl)acetamide], bis(trimethylsilyl)urea or the like; a derivative formed by reaction of the compound (IV) with phosphorus trichloride or phosgene, and the like.

Suitable reactive derivative at the carboxy group of the compound (VIII) may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 1-hydroxy-1H-benzotriazole, 4-substituted imidazole, dimethylpyrazole, triazole or tetrazole; or an activated ester [e.g. cyanomethyl ester, methoxymethyl ester, dimethyliminomethyl [$(CH_3)_2 \overset{+}{N}=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, benzothiazolyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (VIII) to be used.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (VIII) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonyl-bis(2-methylimidazole); pentamethyleneketene-N-cyclohexylimine; diphenylketene-N-cyclohexylimine, ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

Process (5)

The compound (Ic) or a salt thereof can be prepared by subjecting the compound (Ib) or a salt thereof to elimination reaction of the hydroxy protective group. Suitable method of this reaction may include conventional one such as hydrolysis, reduction and the like.

(i) For Hydrolysis:

The hydrolysis is preferably carried out in the presence of a base or an acid including Lewis acid.

Suitable base may include an inorganic base and an organic base such as an alkali metal [e.g. sodium, potassium, etc.], the hydroxide or carbonate or bicarbonate thereof, alkali metal lower alkoxide (e.g. sodium methoxide, sodium ethoxide, etc.], hydrides [e.g. lithium aluminum hydride, etc.], trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

(ii) For reduction:

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like. The reduction is usually carried out in a conventional solvent which does not adversely influence the reaction such as water, methanol, ethanol, propanol, N,N-dimethylformamide, tetrahydrofuran, or a mixture thereof. Additionally, in case that the above-mentioned acids to be used in chemical reduction are in liquid, they can also be used as a solvent.

The reaction temperature of this reduction is not critical and the reaction is usually carried out under cooling to warming.

Process (6)

The compound (Ie) or a salt thereof can be prepared by subjecting the compound (Id) or its reactive derivative at the amino group or a salt thereof to acylation reaction.

Suitable acylating agent to be used in the present acylation reaction may include the compound of the formula:

$$R^{12}-OH \qquad (XXXV)$$

(wherein $R^{12}$ is acyl)
or its reactive derivative or a salt thereof.

Suitable reactive derivative at the amino group of the compound (Id) may include Schiff's base type imino or its tautomeric enamine type isomer formed by the reaction of the compound (Id) with a carbonyl compound such as aldehyde, ketone or the like; a silyl derivative formed by the reaction of the compound (Id) with a silyl compound such as N,O-bis(trimethylsilyl)acetamide, N-trimethylsilylacetamide or the like; a derivative formed by the reaction of the compound (Id) with phosphorus trichloride or phosgene, and the like.

Suitable reactive derivative of the compound (XXXV) may include an acid halide, an acid anhydride, an activated amide, an activated ester, isocyanate, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosporous acid, sulfurous acid, thiosulfuric acid, alkanesulfonic acid (e.g. methanesulfonic acid, ethanesulfonic acid, etc.), sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl $[(CH_3)_2 \overset{+}{N}=CH-]$ ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.); substituted or unsubstituted aryl isocyanate; substituted or unsubstituted aryl isothiocyanate, and the like. These reactive derivatives can optionally be selected from them according to the kind of the compound (XXXV) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (XXXV) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methylimidazole); pentamethyleneketene-ethoxyacetylene; 1-alkoxy-1- chloroethylene; trialkyl phosphite; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)- 6-chloro-1H-benzotriazole; so-called Vilsmeier reagent prepared by the reaction of N,N-dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine (e.g. triethylamine, diisopropylethylamine, etc.), pyridine, N-(lower)alkylmorphorine, N,N-di(lower)alkylbenzylamine, or the like. The reaction temperature is not critical, and the reaction is usually carried out under cooling to heating.

Process (7)

The compound (Id) or a salt thereof can be prepared by subjecting the compound (Ie) or a salt thereof to deacylation reaction.

This reaction can be carried out in a similar manner to that of the aforementioned Process (5), and therefore the reagents to be used and the reaction conditions (e.g., solvent, reaction temperature, etc.) can be referred to those of the Process (5).

Process (8)—①

The compound (XXIII) or a salt thereof can be prepared by reacting the compound (IV) or a salt thereof with the compound (XXII) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, diethyl ether or any other solvent which does not adversely affect the reaction.

The reaction temperature is not critical and the reaction is usually carried out under cooling to heating.

Process (8)—②

The compound (If) or a salt thereof can be prepared by reacting the compound (XXIII) or a salt thereof with the compound (XXIV) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, diethyl ether or any other solvent which does not adversely affect the reaction.

The reaction temperature is not critical and the reaction is usually carried out under cooling to heating.

Process (A)—①

The compound (XI) can be prepared by reacting the compound (IX) with the compound (X).

This reaction can be carried out in accordance with the method disclosed in the Preparation 1 described later or a similar manner thereto.

Process (A)—②

The compound (XII) or a salt thereof can be prepared by subjecting the compound (XI) to reduction reaction.

This reduction can be carried out in accordance with the method disclosed in the Preparation 2 described later or a similar manner thereto.

Process (B)

The compound (XIV) or a salt thereof can be prepared by subjecting the compound (XIII) or a salt thereof to elimination reaction of the carbonyl protective group.

This reaction can be carried out in accordance with the method disclosed in the Preparation 3 described later or a similar manner thereto.

Process (C)

The compound (XVa) or a salt thereof can be prepared by reacting the compound (XIV) or its reactive derivative at the amino group, or a salt thereof with the compound (VIII) or its reactive derivative at the carboxy group, or a salt thereof.

This reaction can be carried out in a similar manner to that of the aforementioned Process (4), and therefore the reagents to be used and the reaction conditions (e.g., solvent, reaction temperature, etc.) can be referred to those of the Process (4).

Process (D)

The compound (IIa) or a salt thereof can be prepared by subjecting the compound (XV) or a salt thereof to halogenation reaction.

This halogenation is usually carried out by using a conventional halogenating agent such as halogen (e.g. chlorine, bromine, etc.), phosphorus trihalide (e.g. phosphorus tribromide, phosphorus trichloride, etc.), phosphorus pentahalide (e.g. phosphorus pentachloride, phosphorus pentabromide, etc.), phosphorus oxychloride, thionyl halide (e.g. thionyl chloride, thionyl bromide, etc.) and the like.

This reaction is usually carried out in a solvent such as alcohol (e.g., methanol, ethanol, etc.), benzene, dioxane, N,N-dimethylformamide, tetrahydrofuran, methylene chloride, ethylene chloride, chloroform, diethyl ether or any other solvent which does not adversely affect the reaction.

The reaction temperature is not critical and the reaction is usually carried out under cooling to warming.

Process (E)

The compound (XVII) or a salt thereof can be prepared by reacting the compound (IIa) or a salt thereof with the compound (XVI) or a salt thereof.

The reaction is usually carried out in a conventional solvent such as alcohol (e.g., methanol, ethanol, etc.), tetrahydrofuran, N,N-dimethylformamide, dichloromethane, acetic acid, or any other solvent which does not adversely influence the reaction.

The reaction temperature is not critical and the reaction is usually carried out under warming to heating.

Process (F)—①

The compound (XIX) or a salt thereof can be prepared by reacting the compound (XVIIa) or a salt thereof with the compound (XVIII) or a salt thereof.

The reaction is usually carried out in a conventional solvent such as water, alcohol (e.g., methanol, ethanol, isopropyl alcohol, t-butyl alcohol, etc.), acetone, tetrahydrofuran, dioxane, dichloromethane, chloroform, dimethyl acetamide, N,N-dimethylformamide or any other organic solvent which does not adversely influence the reaction. Among these solvents, hydrophilic solvents may be used in a mixture with water.

The reaction temperature is not critical and the reaction is usually carried out under cooling to warming.

Process (F)—②

The compound (XX) or a salt thereof can be prepared by reacting the compound (XIX) or a salt thereof to deacylation.

This reaction is carried out in accordance with a conventional method such as hydrolysis, reduction or the like.

This reaction can be carried out in a similar manner to that of the aforementioned Process (5) and therefore the reagents to be used and the reaction conditions (e.g., solvent, reaction temperature, etc.) can be referred to those of the Process (5).

Process (F)—③

The compound (VI) or a salt thereof can be prepared by reacting the compound (XX) or a salt thereof with the compound (XXI).

The reaction is usually carried out in a conventional solvent such as water, alcohol (e.g., methanol, ethanol, isopropyl alcohol, t-butyl alcohol, etc.), tetrahydrofuran, dioxane, dichloromethane, chloroform, dimethyl acetamide, N,N-dimethylformamide or any other organic solvent which does not adversely influence the reaction. Among these solvents, hydrophilic solvents may be used in a mixture with water.

The reaction temperature is not critical and the reaction is usually carried out under cooling to warming.

Process (G)

The compound (IV) or a salt thereof can be prepared by reacting the compound (Ig) or a salt thereof to deacylation.

This reaction is carried out in accordance with a conventional method such as hydrolysis, reduction or the like.

This reaction can be carried out in a similar manner to that of the aforementioned Process (5) and therefore the reagents to be used and the reaction conditions (e.g., solvent, reaction temperature, etc.) can be referred to those of the Process (5).

Process (H)—①

The compound (XXVII) or a salt thereof can be prepared by reacting the compound (XXV) or a salt thereof with the compound (XXVI).

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, diethyl ether or any other solvent which does not adversely affect the reaction.

The reaction temperature is not critical and the reaction is usually carried out under cooling to heating.

Process (H)—②

The compound (XXVIII) or a salt thereof can be prepared by subjecting the compound (XXVII) or a salt thereof to amidation reaction.

This reaction can be carried out in accordance with the method disclosed in the Preparations 16 and 19 described later or similar manners thereto.

Process (I)

The compound (XXIX) or a salt thereof can be prepared by reacting the compound (XXVIII) or its reactive derivative at the amino group, or a salt thereof with the compound (VIII) or its reactive derivative at the carboxy group, or a salt thereof.

This reaction can be carried out in a similar manner to that of the aforementioned Process (4), and therefore the reagents to be used and the reaction conditions (e.g., solvent, reaction temperature, etc.) can be referred to those of the Process (4).

Process (J)

The compound (XXXII) or a salt thereof can be prepared by reacting the compound (XXX) or a salt thereof with the compound (XXXI).

This reaction is usually carried out in a solvent such as benzene, tetrahydrofuran, toluene, methylene chloride, ethylene dichloride, chloroform, diethyl ether or any other solvent which does not adversely affect the reaction.

The reaction temperature is not critical and the reaction is usually carried out under cooling to heating.

Process (K)

The compound (II) or a salt thereof can be prepared by reacting the compound (XXXIII) or a salt thereof with the compound (XXXIV) or a salt thereof.

This reaction can be carried out in accordance with the method disclosed in the Preparation 17 described later or a similar manner thereto.

Suitable salts of the object and starting compounds and their reactive derivatives in Processes (1)–(8) and (A)–(K) can be referred to the ones as exemplified for the compound (I).

The compounds obtained by the above Processes (1)–(8) and (A)–(K) can be isolated and purified by a conventional method such as pulverization, recrystallization, column chromatography, reprecipitation or the like.

It is to be noted that each of the object compound (I) may include one or more stereoisomer such as optical isomer(s) and geometrical isomer(s) due to asymmetric carbon atom(s) and double bond(s) and all such isomers and mixture thereof are included within the scope of this invention.

The new thiazole derivatives (I) and pharmaceutically acceptable salts thereof possess antiulcer activity and $H_2$-receptor antagonism, and are useful for a prophylactic or therapeutic treatment of gastritis, ulcer (e.g. gastric ulcer, duodenal ulcer, anastomotic ulcer, etc.), Zollinger-Ellison Syndrome, reflux esophagitis, upper gastrointestinal bleeding, and the like.

And further, the compound (I) and pharmaceutically acceptable salts thereof of the present invention possess high antimicrobial activity against pathogenic microorganisms such as Helicobacter pylori, which is a gram-negative bacillus that has recently been found beneath the mucus gel of the human stomach. Actually, the compound (I) of the present invention inhibited the growth of *Helicobacter pylori*.

The object compound (I) or its pharmaceutically acceptable salts can usually be administered to mammals including human being in the form of a conventional pharmaceutical composition such as oral dosage form (e.g., capsule, microcapsule, tablet, granule, powder, troche, syrup, aerosol, inhalation, suspension, emulsion, etc.), injection dosage form or suppository, or the like.

The pharmaceutical composition of this invention can contain various organic or inorganic carrier materials, which are conventional used for pharmaceutical purpose, such as excipient (e.g. sucrose, starch, mannit, sorbit, lactose, glucose, cellulose, talc, calcium phosphate, calcium carbonate, etc.), binding agent (e.g. cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropylstarch, sodium glycole-starch, sodium bicarbonate, calcium phosphate, calcium citrate, etc.), lubricant (e.g. magnesium stearate, talc, sodium laurylsulfate, etc.), flavoring agent (e.g. citric acid, mentol, glycine, orange powders, etc.), preservative (e.g. sodium benzoate, sodium bisulfite, methylparaben, propylparaben, etc.), stabilizer (e.g. citric acid, sodium citrate, acetic acid, etc.), suspending agent (e.g. methyl cellulose, polyvinylpyrrolidone, aluminum stearate, etc.), dispersing agent, aqueous diluting agent (e.g. water), base wax (e.g. cacao butter, polyethyleneglycol, white petrolatum, etc.).

While the dosage of the compound (I) will vary depending upon the age and condition of the patient, an average single dose of about 0.1 mg, 1 mg, 10 mg, 50 mg, 100 mg, 250 mg, 500 mg and 1000 mg of the compound (I) may be effective for treating ulcer. In general, amounts between 0.1 mg/body and about 1,000 mg/body may be administered per day.

In order to illustrate the usefulness of the object compound (I), the pharmacological test data of some representative compounds of the compound (I) are shown in the following.

Test compounds (a) 4-(3-Ureidomethylphenyl)-2-(diaminomethyleneamino)thiazole (b) 4-(3-Acetylaminomethylphenyl)-2-[[(amino)(methylamino)methylene]amino]thiazole (c) 4-(3-Acetylaminomethylphenyl)-2-[[(amino)(ethylamino)methylene]amino]thiazole Test A (Gastric secretion in Heidenhain pouch dogs):
Test Method Beagle dogs, weighing about 8–13 kg, were used for the study on gastric secretion. The animals were surgically provided with a vagally denervated Heidenhain pouch. One month or more later, the dogs were fasted overnight. Gastric secretion was stimulated by an intravenous infusion of tetragastrin (10 µg/kg/hr). Gastric juice was collected at 15 minutes intervals. After the secretion plateau had been established, test compound (3.2 mg/kg) suspended in 0.1% methyl cellulose solution was administered orally. Gastric juice was collected at 15 minutes intervals over 3 hours period. Acid concentration was determined by titrating an aliquot against 0.1N sodium hydroxide using automatic titrator (Hiranuma RAT-11 Type). Total acid output was calculated by multiplying the volume of gastric juice by acid concentration, and percentage inhibition was calculated by comparing total acid output before adminstration of test compound with that after administration of test compound.

Test Result

| Test Compound | Inhibition (%) |
|---|---|
| (b) | 88.1 |

Test B (Inhibition of stress ulcer):
Test Method

Five male Sprague-Dawley rats, aged 7 weeks, were fasted but allowed free access to water for 24 hours. Animals were placed in a restraint cage and immersed to a level of the xiphoid in a water bath kept 22° C. for 7 hours. Each of the test compounds (32 mg/kg) suspended in 0.1% methylcellulose solution was administered orally just before the stress subjection. Animals were sacrificed and stomachs were removed. After fixing with 2% formalin, stomachs were opened along the greater curvature and area of ulcers was measured. Percentage inhibition was calculated by comparing the mean area of ulcers (mm$^2$) in the test group with that in the control group.

Test Result

| Test Compound | Inhibition (%) |
|---|---|
| (c) | 88.1 |

Test C (Gastric secretion from lumen perfused stomach in anesthetized rats):
Test Method Male Sprague-Dawley rats weighing about 250 g were used. Rats were deprived of food but allowed free access to water for 24 hours. The animals were anesthteized with 1.25 g/kg urethane intraperitoneally. The abdomen was opened and the gastric lumen was perfused with saline throughout the experiment. The perfusate was titrated continuously against 25 mM sodium hydroxide to maintain the perfusate solution at pH 7.0. Gastric secretion was stimulated by intravenous infusion with histamine (3 mg/kg/hr). After reaching plateau, test compound (1 mg/kg) was given intravenously at a volume of 2 ml/kg. Effect of drug was expressed as maximal inhibition of acid output calculated by the amount of sodium hydroxide required.

Test Result

| Test Compound | Inhibition (%) |
|---|---|
| (a) | 99 |

Preferred embodiments of the object compound (I) are as follows.

$R^2$ is hydrogen, or lower alkyl which may have one to three suitable substituent(s) [more preferably lower alkyl which may have one or two substituent(s) selected from the group consisting of lower alkoxy, hydroxy, protected hydroxy, di(lower)alkylamino, heterocyclic group and aryl which may have suitable substituent(s); most preferably lower alkyl which may have lower alkoxy, hydroxy, acyloxy, di(lower)alkylamino, pyridyl, imidazolyl or lower alkoxyphenyl], $R^3$ is hydrogen, lower alkyl, lower alkoxy or halogen, A is $C_1$–$C_4$ alkylene [more preferably methylene], Q is a group of the formula:

—CO—$R^1$ (in which $R^1$ is lower alkyl, amino, protected amino, hydroxy(lower)alkyl, protected hydroxy(lower)alkyl, lower alkoxy, amino(lower)alkyl, or protected amino(lower)alkyl [more preferably lower alkyl, amino, acylamino, hydroxy(lower)alkyl, acyloxy(lower)alkyl, lower alkoxy, amino(lower)alkyl, or acylamino(lower)alkyl; most preferably lower alkyl, amino, acylamino, hydroxy(lower)alkyl, lower alkanoyloxy(lower)alkyl, lower alkoxy, amino(lower)alkyl, lower alkanoylamino(lower)alkyl, or lower alkoxycarbonylamino(lower)alkyl]), or carbamimidoyl which may have one to three suitable substituent(s) [more preferably carbamimidoyl which may have one or two suitable substituent(s) selected from the group consisting of cyano and lower alkyl; [most preferably carbamimidoyl which has cyano and lower alkyl], with proviso that
when Q is carbamimidoyl which may have one to three suitable substituent(s),
then $R^3$ is lower alkoxy.

The following Preparations and Examples are given for the purpose of illustrating the present invention in more detail.

Preparation 1

A suspension of 3-acetylbenzonitrile (50.0 g), ethylene glycol (34.0 g) and boron trifluoride etherate (1 ml) in benzene (200 ml) was heated at 100° C. by means of a Dean-Stark apparatus for 5 hours. After cooling, a saturated aqueous sodium hydrogencarbonate solution (200 ml) was added. The benzene layer was collected and then dried with sodium sulfate. The solvent was removed under reduced pressure to afford 3-(2-methyl-1,3-dioxolan-2-yl)benzonitrile (65.0 g) (oil).

IR (Film): 2970, 2880, 2230, 1580 cm$^{-1}$

NMR (CDCl$_3$, δ): 1.64 (3H, s), 3.73–3.79 (2H, m), 4.04–4.11 (2H, m), 7.46 (1H, td, J=7.7 and 0.5 Hz), 7.59 (1H, dt, J=7.5 and 1.5 Hz), 7.73 (1H, dt, J=7.7 and 1.5 Hz), 7.80 (1H, dt, J=1.5 and 0.5 Hz)

Preparation 2

A solution of 3-(2-methyl-1,3-dioxolan-2-yl)benzonitrile (65.6 g) in tetrahydrofuran (400 ml) was added to a suspension of lithium aluminum hydride (26.3 g) in tetrahydrofuran (400 ml) with cooling on an ice-water bath under nitrogen stream for 1 hour. The mixture was stirred at room temperature for 2 hours. Ethyl acetate (200 ml) was added slowly with cooling on an ice bath and then ice-water (200 ml) was added very slowly with cooling on an ice bath. The resulting precipitate was removed by filtration. The solvent was removed under reduced pressure. Chloroform (300 ml) was added to the residue. The mixture was washed with water (100 ml) and then dried with magnesium sulfate. The solvent was removed under reduced pressure to afford 3-(2-methyl-1,3-dioxolan-2-yl)benzylamine (57.2 g) (oil).

IR (Film): 3300, 2980, 2880, 1650 cm$^{-1}$

NMR (CDCl$_3$, δ): 1.66 (3H, s), 3.75–3.82 (2H, m), 3.88 (2H, s), 4.01–4.08 (2H, m), 7.23–7.42 (4H, m)

Preparation 3

A solution of 3-(2-methyl-1,3-dioxolan-2-yl)benzylamine (57.2 g) in 1N hydrochloric acid (500 ml) and methanol (500 ml) was stirred at room temperature for 2 hours. The solvent was removed under reduced pressure. The residue was dissolved in methanol. The resulting precipitate was removed by filtration. The solvent was removed under reduced pressure. Recrystallization from a mixture of ethanol and acetone afforded 3-acetylbenzylamine hydrochloride (31.2 g).

mp: 145°–146° C.

IR (Nujol): 3180, 1680, 1610 cm$^{-1}$

NMR (DMSO-d$_6$, δ): 2.61 (3H, s), 4.11 (2H, s), 7.58 (1H, t, J=7.7 Hz), 7.76 (1H, d, J=7.7 Hz), 7.97 (1H, d, J=7.7 Hz), 8.15 (1H, s), 8.50 (3H, br s)

Preparation 4

Acetyl chloride (2.5 g) was added slowly to a suspension of 3-acetylbenzylamine hydrochloride (5.0 g) and triethylamine (6.0 g) in dichloromethane (50 ml) with cooling on an ice-water bath. The mixture was stirred at room temperature for 10 hours. The solvent was removed under reduced pressure. The residue was dissolved in water (100 ml). The solution was alkalified with an aqueous potassium carbonate solution. The mixture was extracted with ethyl acetate (150 ml). The solution was dried with magnesium sulfate. The solvent was removed under reduced pressure to afford 3'-acetylaminomethylacetophenone (3.2 g) (oil).

IR (Film): 3250, 3070, 1680, 1640 cm$^{-1}$

NMR (DMSO-d$_6$, δ): 1.88 (3H, s), 2.57 (3H, s), 4.31 (2H, d, J=6.0 Hz), 7.43–7.54 (2H, m), 7.82–7.87 (2H, m), 8.43 (1H, t, J=6.0 Hz)

Preparation 5

Conc. hydrochloric acid (10 ml) was added slowly to a suspension of 4-(3-acetylaminomethylphenyl)-2-(diaminomethyleneamino)thiazole (2.8 g) in ethanol (100 ml). The mixture was refluxed for 18 hours. After cooling, the resulting precipitate was collected by filtration to afford 4-(3-aminomethylphenyl)-2-(diaminomethyleneamino)thiazole dihydrochloride (1.75 g).

mp: 219°–220° C. (dec.)

IR (Nujol): 3300, 1680, 1605 cm$^{-1}$

NMR (DMSO-d$_6$, δ): 4.09 (2H, q, J=5.4 Hz), 7.47 (2H, d, J=4.9 Hz), 7.79 (1H, s), 7.94–7.97 (1H, m), 8.25 (1H, s), 8.38 (4H, s), 8.61 (3H, br), 12.80 (1H, br)

Preparation 6

The following compound was obtained according to a similar manner to that of Example 1 as mentioned below.

4-(3-Acetylaminomethylphenyl)-2-aminothiazole mp: 172°–173° C.

IR (Nujol): 3300, 3120, 1640, 1610 cm$^{-1}$

NMR (DMSO-d$_6$, δ): 1.87 (3H, s), 4.26 (2H, d, J=5.9 Hz), 6.97 (1H, s), 7.06 (2H, s), 7.13 (1H, d, J=7.6 Hz), 7.30 (1H, t, J=7.6 Hz), 7.64–7.68 (2H, m), 8.35 (1H, t, J=5.9 Hz)

Preparation 7

A suspension of 4-(3-acetylaminomethylphenyl)-2-aminothiazole (2.0 g) and benzoyl isothiocyanate (1.32 g) in acetone (40 ml) was refluxed for 5 hours. The resulting precipitate was collected by filtration to afford 4-(3-acetylaminomethylphenyl)-2-(3-benzoyl-2-thioureido)thiazole (2.94 g).

mp: 225°–226° C. (dec.)

IR (Nujol): 3260, 1680, 1640 cm$^{-1}$

NMR (DMSO-d$_6$, δ): 1.89 (3H, s), 4.31 (2H,, d, J=5.9 Hz), 7.24 (1H, d, J=7.7 Hz), 7.40 (1H, t, J=7.6 Hz), 7.57 (2H, t, J=7.7 Hz), 7.67–7.84 (4H, m), 8.03 (2H, dd, J=1.5 and 7.1 Hz), 8.41 (1H, t, J=5.9 Hz), 12.21 (1H, s), 14.27 (1H, s)

Preparation 8

Aqueous sodium hydroxide solution (0.5 g in 4 ml water) was added to a suspension of 4-(3-acetylaminomethylphenyl)-2-(3-benzoyl-2-thioureido)thiazole (2.0 g) in methanol (40 ml). The mixture was heated at 60° C. for 8.5 hours. The solvent was removed under reduced pressure. The residue was dissolved in water (50 ml). The mixture was neutralized with 6N-hydrochloric acid. The resulting precipitate was collected by filtration to afford 4-(3-acetylamino-methylphenyl)-2-thioureidothiazole (2.0 g).

mp: 228°–230° C.

IR (Nujol): 3400, 3300, 1620 cm$^{-1}$

NMR (DMSO-d$_6$, δ): 1.89 (3H, s), 4.29 (2H, d, J=5.9 Hz), 7.20 (1H, d, J=7.6 Hz), 7.37 (1H, t, J=7.6 Hz), 7.50 (1H, s), 7.73 (1H, d, J=7.6 Hz), 7.74 (1H, s), 8.37 (1H, t, J=5.9 Hz), 8.78 (1H, br), 11.73 (1H, s)

Preparation 9

A suspension of 4-(3-acetylaminomethylphenyl)-2-thioureidothiazole (5.75 g) and methyl iodide (3.73 g) in methanol (100 ml) was refluxed for 2.5 hours. The solvent was removed under reduced pressure. The residue was crystallized from a mixture of methanol and ethyl acetate to afford 4-(3-acetylaminomethylphenyl)-2-(2-methyl-1-isothioureido)thiazole hydriodide (6.3 g).

mp: 114°–115° C. (dec.)

IR (Nujol): 3250, 1630 cm$^{-1}$

NMR (DMSO-d$_6$, δ): 1.89 (3H, s), 2.56 (3H, s), 4.30 (2H, d, J=5.8 Hz), 7.23 (1H, d, J=7.7 Hz), 7.40 (1H, t, J=7.7 Hz), 7.66 (1H, s), 7.75–7.76 (2H, m), 8.39 (1H, t, J=5.8 Hz), 9.53 (1H, br)

Preparation 10

A suspension of 4-(3-acetylaminomethylphenyl)-2-amino(2-methoxyethylamino)methyleneamino]thiazole (5.5 g) in concentrated hydrochloric acid (10 ml) and ethanol (100 ml) was refluxed for 16 hours. After cooling, acetone was added. The mixture was stirred at room temperature and then the resulting precipitate was collected by filtration. Recrystallization from ethanol afforded 4-(3-aminomethylphenyl)-2-[[(amino)(2-methoxyethylamino)methylene]amino]thiazole dihydrochloride (5.55 g).

mp: 240°–242° C. (dec.)

IR (Nujol): 3350, 1680, 1620 cm$^{-1}$

NMR (DMSO-d$_6$, δ): 3.36 (3H, s), 3.62 (4H, br), 3.95–4.18 (2H, br), 7.49–7.51 (2H, m), 7.77 (1H, s), 7.85–8.05 (1H, m), 8.17 (1H, br s), 8.60 (4H, br), 9.45–9.70 (1H, br), 12.75–12.97 (1H, br)

Preparation 11

The following compound was obtained according to a similar manner to that of Preparation 10.

2-[(Amino)(2-hydroxyethylamino)methyleneamino]-4(3-aminomethylphenyl)thiazole dihydrochloride mp: 219°–220° C. (dec.)

IR (Nujol): 3350, 1680, 1610 cm$^{-1}$

NMR (DMSO-d$_6$, δ): 3.50–3.80 (4H, m), 4.07 (2H, d, J=5.5 Hz), 4.29 (1H, br), 7.47–7.50 (2H, m), 7.79 (1H, s), 7.90–8.05 (1H, m), 8.21 (1H, br s), 8.35–9.00 (5H, br), 9.73 (1H, br), 12.95 (1H, br)

Preparation 12

The following compound was obtained according to a similar manner to that of Preparation 5.

4-(3-Aminomethyl-4-methoxyphenyl)-2-(diaminomethyleneamino)thiazole

NMR (DMSO-$d_6$, $\delta$): 3.69 (2H, s), 3.81 (3H, s), 6.96–6.87 (6H, m), 7.65 (1H, dd, J=2.2 and 8.4 Hz ), 7.77 ( 1H, d, J=2.2 Hz )

Preparation 13

To a solution of N-(3-cyanobenzyl)acetamide (7.7 g) in methylene dichloride (150 ml) and tetrahydrofuran (50 ml) was added dropwise a solution of methyl magnesium bromide in ether (3 mol/l, 52 ml) at 10° to 20° C. under stirring and the resulting mixture was stirred at the same condition for 6 hours. The reaction mixture was poured into water and the resultant mixture was adjusted to pH 7 with 6N hydrochloric acid and extracted with ethyl acetate. The extract was washed with brine and magnesium sulfate. The solvent was evaporated in vacuo and the residue was subjected to column chromatography on silica gel. The fractions eluted with a mixture of chloroform and ethyl acetate (8:2) were collected and the solvent was evaporated in vacuo to give 3'-(acetylaminomethyl)acetophenone (4.7 g) (oil).

NMR (DMSO-$d_6$, $\delta$): 1.91 (3H, s), 2.57 (3H, s), 4.34 (2H, m), 7.43–7.92 (4H, m), 8.44 (1H, m)

Preparation 14

The following compound was obtained according to a similar manner to that of Example 1.

4-(3-Acetylaminomethylphenyl)-2-thioureidothiazole

Preparation 15

A solution of 3-cyanobenzyl chloride (13.3 g) in N,N-dimethylformamide (30 ml) was added dropwise to a suspension of potassium phthalimide (15.9 g) in N,N-dimethylformamide (160 ml) at ambient temperature under stirring and the resultant mixture was stirred for 12 hours at ambient temperature. The reaction mixture was poured into water and the precipitate was collected by filtration. The precipitate was dissolved in a mixture of ethyl acetate and tetrahydrofuran and the resultant solution was washed with brine and dried over magnesium sulfate. The solvent was concentrated in vacuo and the precipitate was collected by filtration to give N-(3-cyanobenzyl)phthalimide (17.1 g).

mp: 147°–149° C.

IR (Nujol): 2220, 1765, 1700, 1605, 1580 cm$^{-1}$

NMR (DMSO-$d_6$, $\delta$): 4.85 (2H, s), 7.52–7.96 (8H, m)

Preparation 16

A solution of hydrazine hydrate (4.0 g) in methanol was added dropwise to a mixture of N-(3-cyanobenzyl)phthalimide (17.0 g) in tetrahydrofuran (150 ml) and methanol (120 ml) at ambient temperature under stirring and the resultant mixture was stirred for 3 hours at ambient temperature. To the reaction mixture was added dropwise 6N-hydrochloric acid (25 ml) and the mixture was stirred for one hour at ambient temperature. The reaction mixture was evaporated in vacuo. To the residue was added water (60 ml) and the mixture was stirred at 10 minutes and filtrated. The filtrate was washed with ethyl acetate and adjusted to pH 8.0 with 20% potassium carbonate solution. Acetic anhydride (15 ml) was added dropwise to the resulting solution at 8° to 20° C. under stirring and the mixture was stirred for one hour at 10° to 20° C. The reaction mixture was extracted with ethyl acetate, and extract was washed with brine and dried over magnesium sulfate. The solvent was evaporated in vacuo and the residue was recrystallized from a mixture of ethyl acetate and diisopropyl ether to give N-(3-cyanobenzyl)acetamide (7.45 g).

mp: 94°–96° C.

IR (Nujol): 3280, 2220, 1640, 1540 cm$^{-1}$

NMR (DMSO-$d_6$, $\delta$): 1.90 (3H, s), 4.30 (2H, d, J=6 Hz), 7.49–7.62 (2H, m), 7.65–8.93 (2H, m), 8.43 (1H, m)

Preparation 17

Chloroacetyl chloride (17 g) was added dropwise to a mixture of aluminum chloride (13.3 g) in dichloroethane (60 ml) at ambient temperature under stirring and the mixture was stirred for one hour. To the resulting mixture was added N-(2-methylbenzyl)acetamide (13.3 g) at ambient temperature and the mixture was stirred at 25° to 50° C. for 1.5 hours. The reaction mixture was poured into ice water and extracted with a mixture of ethyl acetate and tetrahydrofuran. The extract was washed with brine and dried over magnesium sulfate. The solvent was concentrated in vacuo and the residue was washed with ethyl acetate and diisopropyl ether to give N-(4-chloroacetyl-2-methylbenzyl)acetamide (5.8 g).

IR (Nujol): 3280, 1690, 1640, 1550 cm$^{-1}$

NMR (DMSO-$d_6$, $\delta$): 1.89 (3H, s), 2.35 (3H, s), 4.27 (2H, d, J=5.7 Hz), 5.14 (2H, s), 7.34 (1H, d, J=8.4 Hz), 7.80 (2H, m), 8.32 (1H, m)

Preparation 18

A solution of 3'-chloromethyl-4'-methoxyacetophenone (10.0 g) in N,N-dimethylformamide (30 ml) was added slowly to a suspension of potassium phthalimide (9.4 g) in N,N-dimethylformamide (70 ml) at room temperature and then the mixture was stirred for 9 hours at room temperature. After removed of the insoluble material, the solvent was removed under reduced pressure. The residue was suspended in water (100 ml). The mixture was extracted with ethyl acetate (300 ml). The extract was dried with magnesium sulfate. The solvent was removed under reduced pressure to afford 3'-phthalimidomethyl-4'-methoxyacetophenone (11.94 g).

IR (Nujol): 1620 cm$^{-1}$

NMR (DMSO-$d_6$, $\delta$): 2.47 (3H, s), 3.91 (3H, s), 4.77 (2H, s), 7.14 (1H, d, J=8.6 Hz), 7.62 (1H, d, J=2.0 Hz), 7.82–7.98 (5H, m)

Preparation 19

Hydrazine hydrate (3.06 g) was added to a suspension of 3'-phthalimidomethyl-4'-methoxyacetophenone (15.74 g) in methanol (150 ml) and tetrahydrofuran (150 ml) at room temperature and the mixture was stirred at room temperature for 24 hours. Dilute hydrochloric acid (conc. hydrochloric acid (5 ml) in water (100 ml)) was added slowly to the mixture with cooling and the mixture was stirred at room temperature for 1 hour. The mixture was concentrated. Water (100 ml) was added thereto and the mixture was alkalized to pH 10 with 30% aqueous potassium carbonate solution and extracted with ethyl acetate (300 ml). The extract was dried with magnesium sulfate. The solvent was removed under reduced pressure to afford 3'-aminomethyl-4'-methoxyacetophenone (4.45 g).

IR (Film): 3370, 1670, 1600 cm$^{-1}$

NMR (DMSO-$d_6$, $\delta$): 2.52 (3H, s), 3.66 (2H, s), 3.87 (3H, s), 7.04 (1H, d, J=8.6 Hz), 7.86 (1H, dd, J=2.3 and 8.6 Hz), 7.98 (1H, d, J=2.3 Hz)

Preparation 20

A solution of 3'-aminomethyl-4'-methoxyacetophenone (4.45 g) and acetic anhydride (5.58 g) in methanol (40 ml) and tetrahydrofuran (40 ml) was stirred for 1 hour at room temperature. The solvent was removed under reduced pressure and the residue was dissolved in a saturated aqueous sodium hydrogencarbonate solution (100 ml). The mixture was extracted with ethyl acetate (300 ml). The extract was dried with magnesium sulfate. The solvent was removed under reduced pressure to afford 3'-acetylamino-methyl-4'-methoxyacetophenone (3.59 g).

IR (Nujol): 3290, 1660, 1630, 1600 cm$^{-1}$

NMR (DMSO-d$_6$, δ): 1.89 (3H, s), 2.51 (3H, s), 3.89 (3H, s), 4.23 (2H, d, J=5.9 Hz), 7.09 (1H, d, J=8.6 Hz), 7.76 (1H, d, J=2.2 Hz), 7.92 (1H, dd, J=8.6 and 2.2 Hz), 8.27 (1H, t, J=5.86 Hz)

Example 1

Bromine (0.92 g) was added slowly to a solution of 3'-acetylaminomethylacetophenone (1.0 g) in dioxane (20 ml) at room temperature. The mixture was stirred at room temperature for 2 hours and then was evaporated in vacuo. A suspension of the residue and (diaminomethylene)thiourea (0.65 g) in ethanol (20 ml) was refluxed for 6 hours. After cooling, the resulting precipitate was collected by filtration and then was suspended in water (50 ml). The mixture was alkalified with an aqueous potassium carbonate solution. The resulting precipitate was collected by filtration. Recrystallization from a mixture of methanol, tetrahydrofuran and diisopropyl ether afforded 4-(3-acetylaminomethylphenyl)-2-(diaminomethyleneamino)thiazole (0.66 g).

mp: 248°–249° C. (dec.)

IR (Nujol): 3400, 1670, 1620 cm$^{-1}$

NMR (DMSO-d$_6$, δ): 1.89 (3H, s), 4.29 (2H, d, J=5.9 Hz), 6.95 (4H, s), 7.14–7.17 (2H, m), 7.33 (1H, t, J=7.7 Hz), 7.68–7.71 (2H, m), 8.37 (1H, t, J=5.9 Hz)

Example 2

(1) A solution of 4-(3-aminomethylphenyl)-2-(diaminomethyleneamino)thiazole dihydrochloride (1.5 g) and potassium isocyanate (0.76 g) in water (30 ml) was stirred at room temperature for 8.5 hours. The resulting precipitate was collected by filtration and then suspended in water (50 ml). The mixture was alkalified with an aqueous potassium carbonate solution. The resulting precipitate was collected by filtration. Recrystallization from a mixture of methanol and diisopropyl ether afforded 4-(3-ureidomethylphenyl)-2-(diaminomethyleneamino)thiazole (0.6 g).

mp: 230°–232° C.

IR (Nujol): 3410, 3320, 1630, 1590 cm$^{-1}$

NMR (DMSO-d$_6$, δ): 4.21 (2H, d, J=6.0 Hz), 5.54 (2H, s), 6.43 (1H, t, J=6.0 Hz), 6.92 (4H, s), 7.11 (1H, s), 7.16 (1H, d, J=7.6 Hz), 7.32 (1H, t, J=7.6 Hz), 7.68 (1H, d, J=7.6 Hz), 7.70 (1H, s)

The following compound was obtained according to a similar manner to that of Example 2-(1).

(2) 2-[[(Amino)(2-methoxyethylamino)methylene]amino]-4-(3-ureidomethylphenyl)thiazole mp: 199°–200° C. (dec.)

IR (Nujol): 3400, 3330, 1650, 1600 cm$^{-1}$

NMR (DMSO-d$_6$, δ): 3.31–3.47 (7H, m), 4.21 (2H, d, J=5.9 Hz), 5.53 (2H, s), 6.43 (1H, t, J=5.9 Hz), 7.13–7.18 (2H, br), 7.20–7.60 (3H, m), 7.68–7.71 (2H, br)

Example 3

(1) A solution of 4-(3-acetylaminomethylphenyl)-2-(2-methyl-1-isothioureido)thiazole hydriodide (2.0 g) in 30% methylamine in an ethanol solution (50 ml) was refluxed for 3 days. The solvent was removed under reduced pressure and the residue was suspended in water (60 ml). The mixture was alkalified with an aqueous potassium carbonate solution and then extracted with a mixture of ethyl acetate (150 ml) and tetrahydrofuran (30 ml). The solution was dried with magnesium sulfate and then evaporated in vacuo. The residue was crystallized from ethyl acetate. Recrystallization from ethyl acetate afforded 4-(3-acetylaminomethytphenyl)-2-[[(amino)(methylamino)methylene]amino]thiazole(1.2 g).

mp: 162°–163° C.

IR (Nujol): 3300, 3130, 1620, 1580 cm$^{-1}$

NMR (DMSO-d$_6$, δ): 1.89 (3H, s), 2.76 (3H, d, J=4.8 Hz), 4.28 (2H, d, J=5.9 Hz), 7.13–7.17 (2H, m), 7.33 (1H, t, J=7.6 Hz), 7.49 (2H, br), 7.60–7.70 (2H, m), 8.37 (1H, t, J=5.9 Hz)

Elemental Analysis Calcd. for C$_{14}$H$_{17}$N$_5$OS: C 55.43, H 5.65, N 23.08

Found: C 55.51, H 5.81, N 22.96

The following compounds were obtained according to a similar manner to that of Example 3-(1).

(2) 4-(3-Acetylaminomethylphenyl)-2-[[(amino)(ethylamino)methylene]amino]thiazole mp: 167°–169° C.

IR (Nujol): 3450, 3280, 1650, 1600 cm$^{-1}$

NMR (DMSO-d$_6$, δ): 1.13 (3H, t, J=7.1 Hz), 1.89 (3H, s), 3.14–3.28 (2H, m), 4.28 (2H, d, J=5.9 Hz), 7.13 (1H, s), 7.13–7.17 (2H, m), 7.33 (1H, t, J=7.6 Hz), 7.43 (2H, br), 7.66–7.70 (2H, m), 8.36 (1H, t, J=5.9 Hz)

Elemental Analysis Calcd. for C$_{15}$H$_{19}$N$_5$OS: C 56.76, H 6.03, N 22.06

Found: C 56.54, H 6.19, N 21.92

(3) 4-(3-Acetylaminomethylphenyl)-2-[[(amino) (butylamino)methylene]amino]thiazole mp: 154°–155° C.

IR (Nujol): 3320, 3250, 1650, 1600 cm$^{-1}$

NMR (DMSO-d$_6$, δ): 0.92 (3H, t, J=7.0 Hz), 1.31–1.51 (4H, m), 1.88 (3H, s), 3.19 (2H, q, J=6.4 Hz), 4.28 (2H, d, J=5.8 Hz), 7.13–7.17 ( 2H, m), 7.20–7.60 (3H, m), 7.66–7.69 (2H, m), 8.36 (1H, t, J=5.8 Hz)

Elemental Analysis Calcd. for C$_{17}$H$_{23}$N$_5$OS: C 59.10, H 6.71, N 20.27

Found: C 58.97, H 6.93, N 20.50

(4) 4-(3-Acetylaminomethylphenyl)-2-[[(amino)(2-hydroxyethylamino)methylene]amino]thiazole mp: 148°–150° C.

IR (Nujol): 3470, 3320, 1640, 1580 cm$^{-1}$

NMR (DMSO-d$_6$, δ): 1.89 (3H, s), 3.20–3.40 (2H, m), 3.54 (2H, q, J=5.2 Hz), 4.28 (1H, d, J=5.9 Hz), 4.90 (1H, t, J=5.2 Hz), 7.14–7.17 (2H, m), 7.20–7.55 (3H, m), 7.69–7.73 (2H, br), 8.36 (1H, t, J=5.9 Hz)

Elemental Analysis Calcd. for C$_{15}$H$_{19}$N$_5$O$_2$S: C 54.04, H 5.74, N 21.01

Found: C 53.86, H 5.77, N 21.00

Example 4

A solution of acetoxyacetyl chloride (1.08 g) in dichloromethane (10 ml) was added slowly to a suspension of 4-(3-aminomethylphenyl)-2-[[(amino)(2-methoxyethylamino)methylene]amino]thiazole dihydrochloride (2.5 g) and triethylamine (1.60 g) in dichloromethane (40 ml) with cooling on an ice bath. The mixture was stirred at room temperature for 1 day. The solvent was removed under reduced pressure. The residue was suspended in water (100 ml). The mixture was alkalified with an aqueous potassium carbonate solution and then extracted with a mixture of ethyl acetate (250 ml) and tetrahydrofuran (50 ml). The extract was dried with magnesium sulfate and then was evaporated in vacuo. The residue was chromatographed on a silica gel column eluting with a mixture of chloroform and methanol (20:1). The solvent was removed under reduced pressure. The residue was dissolved in methanolic ammonia (50 ml). The mixture was stirred with cooling on an ice-water bath for 1 hour. The solvent was removed under reduced pressure. The residue was dissolved in ethanol (50 ml) and 4N-dioxane solution of hydrogen chloride (10 ml) was added to the mixture. The mixture was stirred at room temperature for 4 hours. The resulting precipitate was collected by filtration. Recrystallization from ethanol afforded 2-[[(amino)(2-methoxyethylamino)methylene]amino]-4-(3-hydroxyacetamidomethylphenyl)thiazole hydrochloride (0.57 g).

mp: 206° to 207° C. (dec.)

IR (Nujol): 3380, 3260, 3190, 3090, 1680, 1670, 1620 cm$^{-1}$

NMR (DMSO-d$_6$, δ): 3.36 (3H, s), 3.62 (4H, s), 3.88 (2H, s), 4.37 (2H, d, J=6.2 Hz), 7.27 (1H, d, J=7.8 Hz), 7.41 (1H, t, J=7.8 Hz), 7.73 (1H, s), 7.77–7.80 (2H, m), 8.33 (1H, t, J=6.2 Hz), 8.51 (2H, br s), 9.61 (1H, br), 12.68 (1H, br)

Example 5

(1) Methyl chloroformate (0.45 g) was added slowly to a suspension of 4-(3-aminomethylphenyl)-2-[[(amino)(2-methoxyethylamino)methylene]amino]thiazole dihydrochloride (1.5 g) and triethylamine (1.6 g) in N,N-dimethylformamide (10 ml) and tetrahydrofuran (10 ml) with cooling on an ice bath. The mixture was stirred at room temperature for 8 hours. Water (100 ml) was added to the mixture. The mixture was extracted with a mixture of ethyl acetate (200 ml) and tetrahydrofuran (20 ml). The extract was dried with magnesium sulfate and then evaporated in vacuo. The residue was chromatographed on a silica gel column eluting with a mixture of chloroform and methanol (20:1). The solvent was removed under reduced pressure and the residue was dissolved in ethanol (20 ml). 4N-Dioxane solution of hydrogen chloride (5 ml) was added to the mixture. The mixture was stirred at room temperature for 30 minutes. The solvent was removed under reduced pressure. The residue was crystallized from a mixture of ethanol and diisopropyl ether. Recrystallization from a mixture of ethanol and diisopropyl ether afforded 2-[[(amino)(2-methoxyethylamino)methylene]amino]-4-(3-methoxycarbonylaminomethylphenyl)thiazole hydrochloride (0.43 g).

mp: 124°–126° C. (dec.)

IR (Nujol): 3300, 3100, 1670, 1610 cm$^{-1}$

NMR (DMSO-d$_6$, δ): 3.38 (3H, s), 3.56 (3H, s), 3.62 (4H, m), 4.25 (2H, d, J=6.1 Hz), 7.26 (1H, d, J=7.7 Hz), 7.42 (1H, t, J=7.7 Hz), 7.72–7.82 (4H, m), 8.50 (2H, s), 9.65 (1H, br), 12.69 (1H, br)

The following compound was obtained according to a similar manner to that of Example 5-(1).

(2) 2-[[(Amino)(2-hydroxyethylamino)methylene]amino]-4-(3-methoxycarbonylaminomethylphenyl)thiazole hydrochloride mp: 211°–212° C. (dec.)

IR (Nujol): 3400, 3320, 3100, 1670, 1650, 1620 cm$^{-1}$

NMR (DMSO-d$_6$, δ): 3.49 (2H, q, J=5.1 Hz), 3.56 (3H, s), 3.60–3.85 (2H, m), 4.24 (2H, d, J=6.1 Hz), 7.24 (1H, d, J=7.7 Hz), 7.39 (1H, t, J=7.7 Hz), 7.70–7.80 (2H, br), 7.80–7.90 (2H, br), 8.42 (2H, br s), 9.78 (1H, br), 12.45 (1H, br)

Example 6

The following compounds were obtained according to a similar manner to that of Example 3-(1).

4-(3-Acetylaminomethylphenyl)-2-[[(amino){2-(pyridin-2-yl)ethylamino}methylene]amino]thiazole mp: 139°–140° C.

IR (Nujol): 3460, 3300, 3050, 1650, 1590 cm$^{-1}$

NMR (DMSO-d$_6$, δ): 1.88 (3H, s), 3.00 (2H, t, J=6.8 Hz), 3.55–3.65 (2H, m), 4.29 (2H, d, J=5.9 Hz), 7.14–7.37 (5H, m), 7.49 (2H, br s), 7.63–7.76 (3H, m), 8.36 (1H, t, J=5.9 Hz), 8.50–8.54 (1H, m)

(2) 4-(3-Acetylaminomethylphenyl)-2-[[(amino){2-(imidazol-5-yl)ethylamino}methylene]amino]thiazole mp: 163°–164° C.

IR (Nujol): 3370, 3320, 3130, 1640, 1620, 1580 cm$^{-1}$

NMR (DMSO-d$_6$, δ): 1.89 (3H, s), 2.75 (2H, t, J=6.9 Hz), 3.41–3.51 (2H, m), 4.29 (2H, d, J=5.8 Hz), 6.85 (1H, s), 7.14–7.17 (2H, m), 7.33 (1H, t, J=7.6 Hz), 7.48 (2H, br), 7.56 (1H, s), 7.64–7.69 (2H, m), 8.39 (1H, t, J=5.8 Hz)

(3) 4-(3-Acetylaminomethylphenyl)-2-[[(amino){2-(4-methoxyphenyl)ethylamino}methylene]amino]thiazole mp: 110°–111° C.

IR (Nujol): 3450, 3300, 1650, 1600 cm$^{-1}$

NMR (DMSO-d$_6$, δ): 1.88 (3H, s), 2.77 (2H, t, J=7.1 Hz), 3.34 (3H, s), 3.39–3.42 (2H, m), 3.71 (3H, s), 4.28 (2H, d, J=5.8 Hz), 6.86 (2H, d, J=8.6 Hz), 7.14–7.21 (3H, m), 7.33 (1H, t, J=7.6 Hz), 7.46 (2H, br), 7.63–7.69 (2H, m), 8.36 (1H, t, J=5.8 Hz)

(4) 4-(3-Acetylaminomethylphenyl)-2-[[(amino)(3-methoxypropylamino)methylene]amino]thiazole mp: 154°–155° C.

IR (Nujol): 3460, 3290, 1650, 1600 cm$^{-1}$

NMR (DMSO-d$_6$, δ): 1.67–1.81 (2H, m), 1.89 (3H, s), 3.23 (2H, q, J=6.5 Hz), 3.24 (3H, s), 3.40 (2H, t, J=6.5 Hz), 4.28 (2H, d, J=5.9 Hz), 7.14–7.17 (2H, br), 7.33 (1H, t, J=7.7 Hz), 7.44 (2H, br s), 7.66–7.69 (2H, br), 8.36 (1H, t, J=5.9 Hz)

Elemental Analysis Calcd. for $C_{17}H_{23}N_5O_2S$: C 56.49, H 6.41, N 19.38

Found: C 56.68, H 6.58, N 19.10

(5) 4-(3-Acetylaminomethylphenyl)-2-[[(amino){2-(dimethylamino)ethylamino}methylene]amino]thiazole mp 138°–140° C.

IR (Nujol): 3460, 3340, 3230, 1630 cm$^{-1}$

NMR (DMSO-d$_6$, δ): 1.88 (3H, s), 2.21 (6H, s), 2.41 (2H, t, J=6.0 Hz), 3.20–3.32 (2H, m), 4.28 (2H, d, J=5.8 Hz), 7.13 (1H, s), 7.15 (1H, d, J=7.6 Hz), 7.20–7.50 (3H, br), 7.69 (1H, s), 7.76 (1H, d, J=7.6 Hz), 8.35 (1H, t, J=5.8 Hz)

Example 7

The following compound was obtained according to a similar manner to that of Example 5-(1).

2-(Diaminomethyleneamino)-4-(3-methyloxycarbonylaminomethylphenyl)thiazole mp: 174°–175° C.

IR (Nujol): 3420, 3310, 1690, 1650, 1610 cm$^{-1}$

NMR (DMSO-d$_6$, δ): 3.56 (3H, s), 4.22 (2H, d, J=6.2 Hz), 6.93 (4H, s), 7.12–7.17 (2H, m), 7.33 (1H, t, J=7.5 Hz), 7.67–7.71 (3H, m)

Example 8

A mixture of N-(4-chloroacetyl-2-methylbenzyl)acetamide (3.6 g) and (diaminomethylene)thiourea (2.3 g) in ethanol (100 ml) was refluxed for 2 hours under stirring. The reaction mixture was evaporated in vacuo and the residue was suspended in water and resultant mixture was adjusted to pH 8.0 with 20% potassium carbonate aqueous solution and the precipitate was collected by filtration. The precipitate was dissolved in a mixture of ethyl acetate and tetrahydrofuran, washed with brine and dried over magnesium sulfate. The solvent was evaporated in vacuo and the residue was recrystallized from ethanol to give 2-(diaminomethyleneamino)-4-(4-acetylaminomethyl-3-methylphenyl)thiazole (3.15 g).

mp: 243°–244° C. (dec.)

IR (Nujol): 3400, 3300, 1660, 1600, 1540 cm$^{-1}$

NMR (DMSO-d$_6$, δ): 1.90 (3H, s), 2.26 (3H, s), 4.26 (2H, d, J=5.5 Hz), 6.93 (4H, m), 7.05 (1H, s), 7.16 (1H, d, J=7.9 Hz), 7.62 (1H, d, J=7.9 Hz), 7.69 (1H, s), 8.23 (1H, m)

Elemental Analysis Calcd. for $C_{14}H_{17}N_5OS$: C 55.43, H 5.65, N 23.08, S 10.57

Found: C 55.08, H 5.69, N 22.99, S 10.60

Example 9

The following compound was obtained according to a similar manner to that of Example 8.

2-(Diaminomethyleneamino)-4-(4-acetylaminomethyl-3-chlorophenyl)thiazole mp: 216°–219° C. (dec.)

IR (Nujol): 3500, 1665, 1580, 1540 cm$^{-1}$

NMR (DMSO-d$_6$, δ): 1.94 (3H, s), 4.35 (2H, d, J=5.7 Hz), 6.96 (4H, m), 7.20 (1H, s), 7.43 (1H, d, J=8.2 Hz), 7.74 (1H, dd, J=8.2 and 1.9 Hz), 7.80 (1H, d, J=1.9 Hz), 8.41 (1H, m)

Example 10

2-(Diaminomethyleneamino)-4-(4-acetylaminomethylphenyl)thiazole was obtained according to a similar manner to that of Example 8.

2-(Diaminomethyleneamino)-4-(4-acetylaminomethylphenyl)thiazole was dissolved in a mixture of methanol (100 ml) and conc. hydrochloric acid (2 ml) and the resulting mixture was evaporated in vacuo and the residue was recrystallized from a mixture of methanol and acetone to give 2-(diaminomethyleneamino)-4-(4-acetylaminomethylphenyl)thiazole dihydrochloride (1.96 g).

mp: 248°–249° C.

IR (Nujol): 1680, 1620, 1545 cm$^{-1}$

NMR (DMSO-d$_6$, δ): 1.89 (3H, s), 4.28 (2H, d, J=6.4 Hz), 7.32 (2H, d, J=8.2 Hz), 7.73 (1H, s), 7.91 (2H, d, J=8.2 Hz), 8.39–8.48 (5H, m), 12.74 (1H, br s)

Example 11

A solution of 4-(3-aminomethyl-4-methoxyphenyl)-2-(diaminomethyleneamino)thiazole (350 mg) and N-[di(methylthio)methylene]cyanamide (190 mg) in N,N-dimethylformamide (20 ml) was heated at 70° C. for 2.5 hours. After cooling, 40% methylamine solution (6 ml) was added to the mixture and the mixture was stirred for 5 hours at room temperature. The solvent was removed under reduced pressure and the residue was chromatographed on a silica gel column eluting with a mixture of chloroform and methanol (10:1). Recrystallization from a mixture of methanol and diisopropyl ether afforded 2-(diamino-methyleneamino)-4-[3-{(3-methyl-2-cyanoguanidino)methyl}-4-methoxyphenyl]thiazole (180 mg).

mp: 238°–240° C. (dec.)

IR (Nujol): 3420, 3300, 2150, 1640 cm$^{-1}$

NMR (DMSO-d$_6$, δ): 2.73 (3H, d, J=4.6 Hz), 3.84 (3H, s), 4.32 (2H, d, J=5.9 Hz), 6.93 (4H, s), 6.95 (1H, s), 7.00 (1H, d, J=8.5 Hz), 7.08 (1H, q, J=4.6 Hz), 7.34 (1H, t, J=5.7 Hz), 7.58 (1H, d, J=2.1 Hz), 7.69 (1H, dd, J=2.1 and 8.5 Hz)

Elemental Analysis Calcd. for C$_{15}$H$_{18}$N$_8$OS: C 50.27, H 5.06, N 31.26

Found: C 50.37, H 4.90, N 30.76

Example 12

A suspension of 2-[[(amino)(2-methoxyethylamino)methylene]amino]-4-(3-aminoacetylaminomethylphenyl)thiazole (270 mg), acetyl chloride (64 mg) and triethylamine (90 mg) in dichloromethane (20 ml) was stirred for 2 hours at room temperature. The solvent was removed under reduced pressure and the residue was dissolved in a mixture of water (50 ml) and tetrahydrofuran (50 ml). The mixture was alkalized to pH 10 with a 30% aqueous potassium carbonate solution and then extracted with ethyl acetate (100 ml). The extract was dried with magnesium sulfate. The solvent was removed under reduced pressure. Recrystallization from a mixture of ethanol and diisopropyl ether afforded 2-[[(amino)(2-methoxyethylamino)methyleneammino]-4-(3-acetylaminoacetylaminomethylphenyl)thiazole (240 mg).

mp: 171°–172° C.

IR (Nujol): 3440, 3200, 1660, 1640, 1590 cm$^{-1}$

NMR (DMSO-d$_6$, δ): 1.87 (3H, s), 3.31–3.47 (7H, m), 3.72 (2H, d, J=5.8 Hz), 4.32 (2H, d, J=5.8 Hz), 7.15 (1H, d, J=7.8 Hz), 7.20 (1H, s), 7.33 (1H, t, J=7.8 Hz), 7.25–7.65 (2H, br), 7.70–7.73 (2H, m), 8.18 (1H, t, J=5.8 Hz), 8.39 (1H, t, J=5.8 Hz)

Elemental Analysis Calcd. for C$_{18}$H$_{24}$N$_6$O$_3$S: C 53.45, H 5.98, N 20.78

Found: C 53.68, H 6.20, N 20.67

Example 13

A suspension of 4-(3-aminomethylphenyl)-2-[[(amino)(2-methoxyethylamino)methylene]amino]thiazole dihydrochloride (3.9 g), N-(t-butoxycarbonyl)glycine (1.85 g), 3-(3-dimethylaminopropyl)-1-ethylcarbodiimide hydrochloride (2.6 g) and triethylamine (2.3 g) in N,N-dimethylformamide (50 ml) was stirred for 7 hours with cooling on an ice bath. The solvent was removed under reduced pressure. The residue was dissolved in a mixture of water (80 ml) and tetrahydrofuran (20 ml), and the mixture was alkalized with 30% aqueous potassium carbonate solution. The mixture was extracted with ethyl acetate (200 ml) and the extract was dried with magnesium sulfate. The solvent was removed under reduced pressure. The residue was chromatographed on a silica gel column eluting with a mixture of chloroform and methanol (20:1) to afford 2-[[(amino)(2-methoxyethylamino)methylene]amino]-4-(3-t-butoxycarbonylaminoacetylaminomethylphenyl)thiazole (1.65 g).

mp: 61°–62° C. (dec.)

IR (Nujol): 3300, 1650 cm$^{-1}$

NMR (DMSO-d$_6$, 67 ): 1.39 (9H, s), 3.25–3.50 (7H, m), 3.58 (2H, d, J=6.0 Hz), 4.32 (2H, d, J=5.8 Hz), 7.04 (1H, t, J=6.0 Hz), 7.15 (1H, d, J=7.8 Hz), 7.20 (1H, s), 7.32 (1H, t, J=7.8 Hz), 7.25–7.50 (2H, br), 7.70–7.73 (2H, br), 8.32 (1H, t, J=5.8 Hz)

Example 14

A solution of 2-[[(amino)(2-methoxyethylamino)methylene]amino]-4-(3-t-butoxycarbonylaminoacetylaminomethylphenyl)thiazole (1.6 g) and 4N-hydrogen chloride/dioxane (10 ml) in methanol (10 ml) was stirred at room temperature for 2.5 hours. The resulting precipitate was collected by filtration and then dissolved in water (50 ml). The mixture was alkalized to pH 10 with a 30% aqueous potassium carbonate solution. The resulting precipitate was collected by filtration. Recrystallization from a mixture of methanol and diisopropyl ether afforded 2-[[(amino)(2-methoxyethylamino)methylene]amino]-4-(3-aminoacetylaminomethylphenyl)thiazole (0.8 g).

mp: 66°–67° C.

IR (Nujol): 3300, 1640, 1590 cm$^{-1}$

NMR (DMSO-d$_6$, δ): 3.15 (2H, s), 3.20–3.55 (7H, m), 4.34 (2H, d, J=5.9 Hz), 7.16–7.19 (2H, br), 7.33 (1H, t, J=7.7 Hz), 7.20–7.60 (2H, br), 7.69–7.72 (2H, br), 8.33 (1H, t, J=5.9 Hz)

Example 15

The following compound was obtained according to a similar manner to that of Example 1.

4-(3-Acetylaminomethyl-4-methoxyphenyl)-2-(diaminomethyleneamino)thiazole mp: 231°–233° C. (dec.)

IR (Nujol): 3400, 1660, 1620 cm$^{-1}$

NMR (DMSO-d$_6$, δ): 1.90 (3H, s), 3.82 (3H, s), 4.23 (2H, d, J=5.7 Hz), 6.70–7.20 (6H, m), 7.62 (1H, d, J=2.1 Hz), 7.69 (1H, dd, J=2.1 and 8.4 Hz), 8.19 (1H, t, J=5.7 Hz)

Elemental Analysis Calcd. for C$_{14}$H$_{17}$N$_5$O$_2$S: C 52.65, H 5.37, N 21.93

Found: C 52.76, H 5.38, N 21.73

Example 16

4N-Hydrogen chloride/dioxane (10 ml) was added to a suspension of 4-(3-acetylaminomethylphenyl)-2-[[(amino)(2-methoxyethylamino)methylene]amino]thiazole (2.0 g) in methanol (20 ml). The mixture was stirred for 3 hours at room temperature. The resulting precipitate was collected by filtration. Recrystallization from water afforded 4-(3-acetylaminomethylphenyl)-2-[[(amino)(2-methoxyethylamino)methylene]amino]thiazole hydrochloride (0.9 g).

mp: 118°–120° C.

IR (Nujol): 3400, 3100, 1670, 1620 cm$^{-1}$

NMR (DMSO-d$_6$, δ): 1.91 (3H, s), 3.37 (3H, s), 3.62 (4H, s), 4.32 (2H, d, J=5.8 Hz), 7.26 (1H, d, J=7.7 Hz), 7.42 (1H, t, J=7.7 Hz), 7.74 (1H, s), 7.81 (2H, br), 8.48 (1H, t, J=5.8 Hz), 8.57 (2H, br s), 9.63 (1H, br), 12.85 (1H, br)

Example 17

A solution of 4-(3-acetylaminomethylphenyl)-2(amino)(2-methoxyethylamino)methylene]amino]thiazole (3.0 g) and methanesulfonic acid (830 mg) in methanol (30 ml) was stirred for 30 minutes at room temperature. The solvent was removed under reduced pressure. The residue was crystallized from a mixture of ethanol and diisopropyl ether. Recrystallization from a mixture of ethanol and diisopropyl ether afforded 4-(3-acetylaminomethylphenyl)-2-[[(amino)(2-methoxyethylamino)methylene]amino]thiazole methanesulfonate (2.3 g).

mp: 167°–168° C.

IR (Nujol): 3270, 3100, 1690, 1620 cm$^{-1}$

NMR (DMSO-d$_6$, δ): 1.90 (3H, S), 2.48 (3H, S), 3.37 (3H, S), 3.61 (4H, br s), 4.32 (2H, d, J=5.8 Hz), 7.26 (1H, d, J=7.7 Hz), 7.42 (1H, t, J=7.7 Hz), 7.75 (1H, s), 7.79–7.82 (2H, m), 8.41 (1H, t, J=5.8 Hz), 8.55 (2H, br s), 9.76 (1H, br), 12.09 (1H, br)

Example 18

Bromine (4.39 g) was added to a solution of 3'-(acetylaminomethyl)acetophenone (5.0 g) in dioxane (50 ml). The mixture was stirred for 4.5 hours at room temperature. The solvent was removed under reduced pressure and the residue containing 3'-(acetylaminomethyl)bromoacetophenone was dissolved in methanol (50 ml). [(2-Methoxyethylamino)(amino)methylene]thiourea (2.5 g) and sodium hydrogencarbonate (13.0 g) were added thereto. The mixture was refluxed for 2 hours. The solvent was removed under reduced pressure. The residue was chromatographed on silica gel column eluting with a mixture of chloroform and methanol (20:1) to afford 4-(3-acetylaminomethylphenyl)-2-[[(amino)(2-methoxyethylamino)methylene]amino]thiazole (0.8 g).

mp: 123°–124° C.

IR (Nujol): 3460, 3280, 3100, 1650, 1630, 1590 cm$^{-1}$

NMR (DMSO-d$_6$, δ): 1.88 (3H, s), 3.31–3.47 (7H, m), 4.28 (2H, d, J=5.9 Hz), 7.13–7.17 (2H, m), 7.30–7.60 (3H, br), 7.70 (2H, br), 8.36 (1H, t, J=5.9 Hz)

Example 19

A solution of 4-(3-acetylaminomethylphenyl)-2-(2-methyl-1-isothioureido)thiazole hydriodide (2.0 g) and 2-methoxyethylamine (5 ml) in ethanol (50 ml) was refluxed for 25 hours. The solvent was removed under reduced pressure and the residue was suspended in water (100 ml). The mixture was alkalized with 30% aqueous potassium carbonate solution and then extracted with a mixture of ethyl acetate (200 ml) and tetrahydrofuran (50 ml). The extract was dried with magnesium sulfate. The solvent was removed under reduced pressure and the residue was crystallized from ethyl acetate. Recrystallization from ethyl acetate afforded 4-(3-acetylaminomethylphenyl)-2-[[(amino)(2-methoxyethylamino)methylene]amino]thiazole (0.65 g).

mp: 123°–124° C.

IR (Nujol): 3460, 3280, 3100, 1650, 1630, 1590 cm$^{-1}$

NMR (DMSO-d$_6$, δ): 1.88 (3H, s), 3.31–3.47 (7H, m), 4.28 (2H, d, J=5.9 Hz), 7.13–7.17 (2H, m), 7.30–7.60 (3H, br), 7.70 (2H, br), 8.36 (1H, t, J=5.9 Hz)

What we claim is:

1. A compound of the formula:

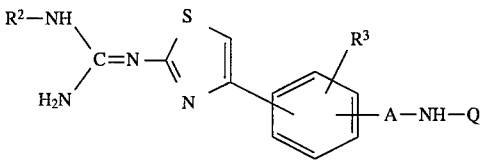

wherein $R^2$ is hydrogen, or lower alkyl which is unsubstituted or substituted by lower alkoxy, hydroxy, acyloxy, di(lower)alkylamino, pyridyl, imidazolyl or lower alkoxyphenyl, $R^3$ is hydrogen, lower alkyl, lower alkoxy, or halogen, A is methylene and Q is a group of the formula:

—CO—$R^1$ (in which $R^1$ is lower alkyl, amino, acylamino, hydroxy(lower)alkyl, lower alkanoyloxy(lower)alkyl, lower alkoxy, amino(lower)alkyl, lower alkanoylamino(lower)alkyl, or lower alkoxycarbonylamino(lower)-alkyl), or carbamimidoyl which is substituted by cyano and lower alkyl, with the proviso that when Q is carbamimidoyl which is substituted by cyano and lower alkyl, then $R^3$ is lower alkoxy.

2. A compound of claim 1, wherein $R^2$ is lower alkyl which may be substituted by pyridyl, imidazolyl or lower alkoxyphenyl, $R^3$ is hydrogen, lower alkyl, lower alkoxy, or halogen, and Q is a group of the formula:

—CO13 $R^1$ wherein $R^1$ is lower alkyl, amino, acylamino, hydroxy(lower)alkyl, acyloxy(lower)alkyl, lower alkoxy, amino(lower)alkyl or acylamino(lower)alkyl.

3. A compound of claim 2, wherein $R^2$ is lower alkoxyphenyl (lower) alkyl, $R^3$ is hydrogen, and Q is a group of the formula:

—CO—$R^1$ wherein $R^1$ is lower alkyl.

4. A pharmaceutical composition which comprises, as an active ingredient, a compound of claim 1 or a pharmaceutically acceptable salt thereof in admixture with pharmaceutically acceptable carriers.

5. A method for the prophylactic or therapeutic treatment of ulcer which comprises administering a compound of claim 1 or a pharmaceutically acceptable salt thereof to human or animals.

* * * * *